United States Patent
Mitchell et al.

(10) Patent No.: US 11,766,550 B2
(45) Date of Patent: Sep. 26, 2023

(54) IMPLANTABLE MEDICATION INFUSION PORT WITH PHYSIOLOGIC MONITORING

(71) Applicant: Veris Health Inc., New York, NY (US)

(72) Inventors: James D. Mitchell, Walnut Creek, CA (US); Andrew A. Thoreson, Orono, MN (US); Theodore C. Johnson, Lake Forest Park, WA (US)

(73) Assignee: Veris Health, Inc., New York, NY (US)

( * ) Notice: Subject to any disclaimer, the term of this patent is extended or adjusted under 35 U.S.C. 154(b) by 869 days.

(21) Appl. No.: 16/614,985

(22) PCT Filed: May 21, 2018

(86) PCT No.: PCT/US2018/033671
§ 371 (c)(1),
(2) Date: Nov. 19, 2019

(87) PCT Pub. No.: WO2018/217633
PCT Pub. Date: Nov. 29, 2018

(65) Prior Publication Data
US 2020/0179669 A1    Jun. 11, 2020

Related U.S. Application Data

(60) Provisional application No. 62/573,148, filed on Oct. 16, 2017, provisional application No. 62/509,156, filed on May 21, 2017.

(51) Int. Cl.
*G08B 21/04* (2006.01)
*A61M 39/02* (2006.01)
(Continued)

(52) U.S. Cl.
CPC ........ *A61M 39/0208* (2013.01); *G16H 10/60* (2018.01); *G16H 20/17* (2018.01); *G16H 40/67* (2018.01); *A61M 2039/0223* (2013.01); *A61M 2205/04* (2013.01); *A61M 2205/3368* (2013.01); *A61M 2205/3507* (2013.01);
(Continued)

(58) Field of Classification Search
USPC ........... 340/539.12, 539.1, 539.22, 588, 589, 340/636.18, 636.1, 693.1, 693.2, 3.3
See application file for complete search history.

(56) References Cited

U.S. PATENT DOCUMENTS 4,834,720 A    5/1989    Blinkhorn
4,846,191 A    7/1989    Brockway et al.
(Continued)

FOREIGN PATENT DOCUMENTS

AU    691877 B2    5/1998
CA    2757836 C    5/2017
(Continued)

OTHER PUBLICATIONS

International Search Report and Written Opinion dated Feb. 18, 2020; International Application No. PCT/US2019/062416; 14 pages.
(Continued)

*Primary Examiner* — Daniel Previl
(74) *Attorney, Agent, or Firm* — Peter D. Sleman; John Colby Van Horn; Coralie L. Wilcox

(57) ABSTRACT

Implantable ports used for intravenous administration and methods of using the same.

21 Claims, 16 Drawing Sheets

(51) Int. Cl.
*G16H 20/17* (2018.01)
*G16H 40/67* (2018.01)
*G16H 10/60* (2018.01)

(52) U.S. Cl.
CPC ... *A61M 2205/52* (2013.01); *A61M 2205/587* (2013.01); *A61M 2205/6054* (2013.01); *A61M 2205/8206* (2013.01); *A61M 2230/06* (2013.01); *A61M 2230/42* (2013.01); *A61M 2230/63* (2013.01)

(56) References Cited

U.S. PATENT DOCUMENTS

| | | |
|---|---|---|
| 4,861,341 A | 8/1989 | Woodburn |
| 4,929,236 A | 5/1990 | Sampson |
| 5,167,638 A | 12/1992 | Felix et al. |
| 5,185,003 A | 2/1993 | Brethauer |
| 5,281,205 A | 1/1994 | Mcpherson |
| 5,360,407 A | 11/1994 | Leonard et al. |
| 5,399,168 A * | 3/1995 | Wadsworth, Jr. ............ A61M 39/0208 604/539 |
| 5,423,334 A | 6/1995 | Jordan |
| 5,476,460 A | 12/1995 | Montalvo |
| 5,558,641 A | 9/1996 | Glantz et al. |
| 5,613,945 A | 3/1997 | Cai et al. |
| 5,620,419 A | 4/1997 | Lui et al. |
| 5,637,102 A | 6/1997 | Tolkoff et al. |
| 5,743,873 A | 4/1998 | Cai et al. |
| 5,833,654 A | 11/1998 | Powers et al. |
| 5,951,512 A | 9/1999 | Dalton |
| 5,989,216 A | 11/1999 | Johnson et al. |
| 6,086,555 A | 7/2000 | Eliasen et al. |
| 6,113,572 A | 9/2000 | Gailey et al. |
| 6,213,973 B1 | 4/2001 | Eliasen et al. |
| 6,478,783 B1 | 11/2002 | Moorehead |
| 6,562,023 B1 | 5/2003 | Marrs et al. |
| 6,650,939 B2 | 11/2003 | Taepke et al. |
| 6,804,558 B2 | 10/2004 | Haller et al. |
| 6,847,844 B2 | 1/2005 | Sun et al. |
| 6,922,592 B2 | 7/2005 | Thompson et al. |
| 6,997,914 B2 | 2/2006 | Smith et al. |
| 7,037,273 B2 | 5/2006 | Zhu et al. |
| 7,069,086 B2 | 6/2006 | Von |
| 7,070,591 B2 | 7/2006 | Adams et al. |
| 7,177,684 B1 | 2/2007 | Kroll et al. |
| 7,181,505 B2 | 2/2007 | Haller et al. |
| D546,440 S | 7/2007 | Burnside |
| D556,153 S | 11/2007 | Burnside |
| 7,324,949 B2 | 1/2008 | Bristol |
| 7,347,843 B2 | 3/2008 | Adams et al. |
| 7,351,233 B2 | 4/2008 | Parks |
| D574,950 S | 8/2008 | Zawacki et al. |
| 7,445,614 B2 | 11/2008 | Bunodiere et al. |
| 7,479,107 B2 | 1/2009 | Zhu et al. |
| 7,713,251 B2 | 5/2010 | Tallarida et al. |
| 7,762,999 B2 | 7/2010 | Byrum |
| 7,775,966 B2 | 8/2010 | Dlugos et al. |
| 7,785,302 B2 | 8/2010 | Powers |
| 7,831,301 B2 | 11/2010 | Webb et al. |
| 7,844,341 B2 | 11/2010 | Von et al. |
| 7,909,769 B2 | 3/2011 | Zhu et al. |
| 7,909,804 B2 | 3/2011 | Stats |
| 7,942,863 B2 | 5/2011 | Kalpin et al. |
| 7,947,022 B2 | 5/2011 | Amin et al. |
| 7,959,615 B2 | 6/2011 | Stats et al. |
| 7,972,314 B2 | 7/2011 | Bizup et al. |
| 8,025,639 B2 | 9/2011 | Powers et al. |
| 8,029,482 B2 | 10/2011 | Maniar et al. |
| 8,092,435 B2 * | 1/2012 | Beling ............ G09F 23/00 604/288.02 |
| 8,140,160 B2 | 3/2012 | Pless et al. |
| 8,147,455 B2 | 4/2012 | Butts et al. |
| 8,175,694 B2 | 5/2012 | Webb et al. |
| 8,177,762 B2 | 5/2012 | Beasley et al. |
| 8,202,259 B2 | 6/2012 | Evans et al. |
| 8,301,254 B2 | 10/2012 | Mosesov et al. |
| D676,955 S | 2/2013 | Orome |
| 8,382,724 B2 | 2/2013 | Maniar et al. |
| 8,391,981 B2 | 3/2013 | Mosesov |
| 8,396,803 B1 | 3/2013 | Dala et al. |
| 8,401,659 B2 | 3/2013 | Von et al. |
| 8,409,221 B2 | 4/2013 | Franklin et al. |
| 8,439,835 B1 | 5/2013 | Mckinley et al. |
| 8,475,417 B2 | 7/2013 | Powers et al. |
| 8,491,547 B2 | 7/2013 | Olsen et al. |
| 8,535,280 B2 | 9/2013 | Mitchell et al. |
| 8,535,281 B2 | 9/2013 | Travis et al. |
| 8,545,460 B2 | 10/2013 | Beasley et al. |
| 8,608,713 B2 | 12/2013 | Beasley et al. |
| 8,608,727 B2 | 12/2013 | Michels et al. |
| 8,615,305 B2 | 12/2013 | Von Arx et al. |
| 8,641,676 B2 | 2/2014 | Butts et al. |
| 8,641,688 B2 | 2/2014 | Powers et al. |
| 8,660,659 B2 | 2/2014 | Mosesov et al. |
| 8,744,581 B2 | 6/2014 | Mosesov |
| 8,805,478 B2 | 8/2014 | Powers et al. |
| 8,827,904 B2 * | 9/2014 | Ball ............ G16H 40/67 600/300 |
| 8,920,389 B2 | 12/2014 | Kalpin et al. |
| 8,920,390 B2 | 12/2014 | Dalton et al. |
| 8,926,573 B2 | 1/2015 | Smith et al. |
| 8,932,271 B2 * | 1/2015 | Hamatake ......... A61M 39/0247 604/288.01 |
| 8,939,947 B2 | 1/2015 | Maniar et al. |
| 9,011,388 B2 | 4/2015 | Schwartz et al. |
| 9,017,256 B2 | 4/2015 | Gottesman |
| 9,072,881 B2 | 7/2015 | Dalton et al. |
| 9,079,004 B2 * | 7/2015 | Wiley ............ A61M 39/0208 |
| 9,101,264 B2 | 8/2015 | Acquista |
| 9,186,455 B2 | 11/2015 | Moyer |
| D748,249 S | 1/2016 | Pittet et al. |
| 9,248,268 B2 | 2/2016 | Wiley et al. |
| 9,327,106 B2 | 5/2016 | Beling et al. |
| 9,358,378 B2 | 6/2016 | Hanson et al. |
| 9,421,352 B2 | 8/2016 | Butts et al. |
| 9,474,888 B2 | 10/2016 | Wiley et al. |
| 9,485,883 B2 | 11/2016 | Koyama |
| 9,498,130 B2 | 11/2016 | Najafi et al. |
| 9,579,496 B2 | 2/2017 | Evans et al. |
| 9,603,992 B2 | 3/2017 | Powers |
| 9,603,993 B2 | 3/2017 | Powers |
| 9,642,556 B2 | 5/2017 | Mo et al. |
| 9,681,825 B2 | 6/2017 | Acquista |
| 9,717,895 B2 | 8/2017 | Wiley et al. |
| 9,814,833 B2 | 11/2017 | Kalpin |
| 9,821,150 B2 | 11/2017 | Pamment |
| 9,937,337 B2 | 4/2018 | Powers et al. |
| 9,950,150 B2 | 4/2018 | Beling et al. |
| 10,016,585 B2 | 7/2018 | Powers et al. |
| 10,022,094 B2 * | 7/2018 | Kerr ............ A61B 6/12 |
| 10,052,470 B2 | 8/2018 | Powers et al. |
| 10,052,471 B2 | 8/2018 | Hamatake et al. |
| 10,086,186 B2 | 10/2018 | Evans et al. |
| 10,155,101 B2 | 12/2018 | Wiley et al. |
| 10,207,095 B2 | 2/2019 | Barron et al. |
| 10,307,581 B2 | 6/2019 | Hibdon et al. |
| 10,321,292 B2 | 6/2019 | Pflugh et al. |
| 11,096,582 B2 | 8/2021 | Mitchell et al. |
| 2001/0027331 A1 | 10/2001 | Thompson |
| 2002/0052539 A1 | 5/2002 | Haller et al. |
| 2002/0193846 A1 | 12/2002 | Pool et al. |
| 2003/0014091 A1 | 1/2003 | Rastegar et al. |
| 2004/0054352 A1 | 3/2004 | Adams et al. |
| 2005/0124980 A1 | 6/2005 | Sanders |
| 2006/0116648 A1 | 6/2006 | Hamatake |
| 2006/0178617 A1 | 8/2006 | Adams et al. |
| 2006/0178648 A1 | 8/2006 | Barron et al. |
| 2007/0016089 A1 | 1/2007 | Fischell et al. |
| 2007/0078391 A1 | 4/2007 | Wortley et al. |
| 2007/0135765 A1 | 6/2007 | Miller et al. |
| 2007/0270672 A1 | 11/2007 | Hayter |
| 2008/0114308 A1 * | 5/2008 | di Palma ............ A61M 39/10 604/533 |

(56) References Cited

U.S. PATENT DOCUMENTS

| | | |
|---|---|---|
| 2009/0118683 A1 | 5/2009 | Hanson et al. |
| 2009/0227951 A1 | 9/2009 | Powers et al. |
| 2010/0191166 A1 | 7/2010 | Phillips et al. |
| 2010/0274221 A1 | 10/2010 | Sigg et al. |
| 2011/0184342 A1 | 7/2011 | Pesach et al. |
| 2011/0202041 A1 | 8/2011 | Forsell |
| 2012/0172711 A1 | 7/2012 | Kerr et al. |
| 2012/0245439 A1 | 9/2012 | Andre et al. |
| 2013/0150811 A1 | 6/2013 | Horgan |
| 2014/0088519 A1 | 3/2014 | Kerr |
| 2014/0207086 A1 | 7/2014 | Stats et al. |
| 2014/0236105 A1 | 8/2014 | Hanson et al. |
| 2014/0249503 A1 | 9/2014 | Bennett et al. |
| 2015/0025478 A1 | 1/2015 | Hibdon et al. |
| 2015/0112315 A1 | 4/2015 | Cudak et al. |
| 2016/0317797 A1* | 11/2016 | Smith ............... A61M 39/0208 |
| 2017/0028185 A1 | 2/2017 | Wiley et al. |
| 2017/0340872 A1 | 11/2017 | Hanson et al. |
| 2018/0043149 A1 | 2/2018 | Martin |
| 2018/0078751 A1 | 3/2018 | Fedor et al. |
| 2018/0103859 A1* | 4/2018 | Provenzano ........... A61B 5/681 |
| 2018/0147343 A1 | 5/2018 | Tyson |
| 2018/0161565 A1 | 6/2018 | Maniar et al. |
| 2018/0177982 A1 | 6/2018 | Albany et al. |
| 2018/0193626 A1 | 7/2018 | Beling et al. |
| 2018/0263511 A1 | 9/2018 | Burnes et al. |
| 2019/0054284 A1 | 2/2019 | Smith et al. |
| 2020/0155003 A1 | 5/2020 | Mitchell et al. |
| 2021/0361166 A1 | 11/2021 | Mitchell et al. |
| 2021/0402164 A1 | 12/2021 | Mitchell et al. |
| 2022/0015708 A1 | 1/2022 | Mitchell et al. |

FOREIGN PATENT DOCUMENTS

| | | |
|---|---|---|
| CN | 104740765 B | 3/2017 |
| DE | 102011078711 A1 | 1/2013 |
| EP | 0392199 A1 | 10/1990 |
| EP | 1391218 A3 | 4/2004 |
| EP | 1413329 B1 | 12/2005 |
| EP | 1773448 A1 | 4/2007 |
| EP | 1962921 A2 | 9/2008 |
| EP | 2020945 B1 | 2/2013 |
| EP | 2859911 A1 | 4/2015 |
| EP | 1874393 B1 | 9/2017 |
| EP | 2416828 B1 | 2/2018 |
| EP | 2501294 B1 | 8/2018 |
| ES | 2041000 T3 | 11/1993 |
| ES | 2041461 T3 | 11/1993 |
| ES | 2136613 T3 | 12/1999 |
| JP | 2000513952 A | 10/2000 |
| JP | 4795523 B2 | 11/2000 |
| JP | 2005169113 A | 6/2005 |
| JP | 4947876 B2 | 3/2012 |
| JP | 2016504158 A | 2/2016 |
| WO | 9934859 A1 | 7/1999 |
| WO | 2010118144 A1 | 10/2010 |
| WO | 2015097255 A2 | 7/2015 |
| WO | 2019118929 A1 | 6/2019 |
| WO | 2020/106890 A1 | 5/2020 |
| WO | 2020106804 A1 | 5/2020 |
| WO | 2020106842 A1 | 5/2020 |
| WO | 2020106890 A1 | 5/2020 |
| WO | 2021102467 | 5/2021 |
| WO | 2022/140766 A1 | 6/2022 |

OTHER PUBLICATIONS

Extended European Search Report dated Nov. 26, 2020; European Patent Application No. 18806546.2; 6 pages.

Dubovitskaya, et al., "Secure and Trustable Electronic Medical Records Sharing using Blockchain", AMAI Annual Symposium Proceedings Achive, Jan. 1, 2017, pp. 650-659.

International Search Report and Written Opinion dated Feb. 18, 2020; International Application No. PCT/US2019/062483; 12 pages.

International Search Report and Written Opinion dated Feb. 24, 2020; International Application No. PCT/US2019/062350; 14 pages.

Kuo et al., "Blockcain distributed ledger technologies for biomedical and health care applications", Journal of the American Medical Informatics Association, vol. 24, No. 6, Sep. 8, 2017, pp. 1211-1220.

* cited by examiner

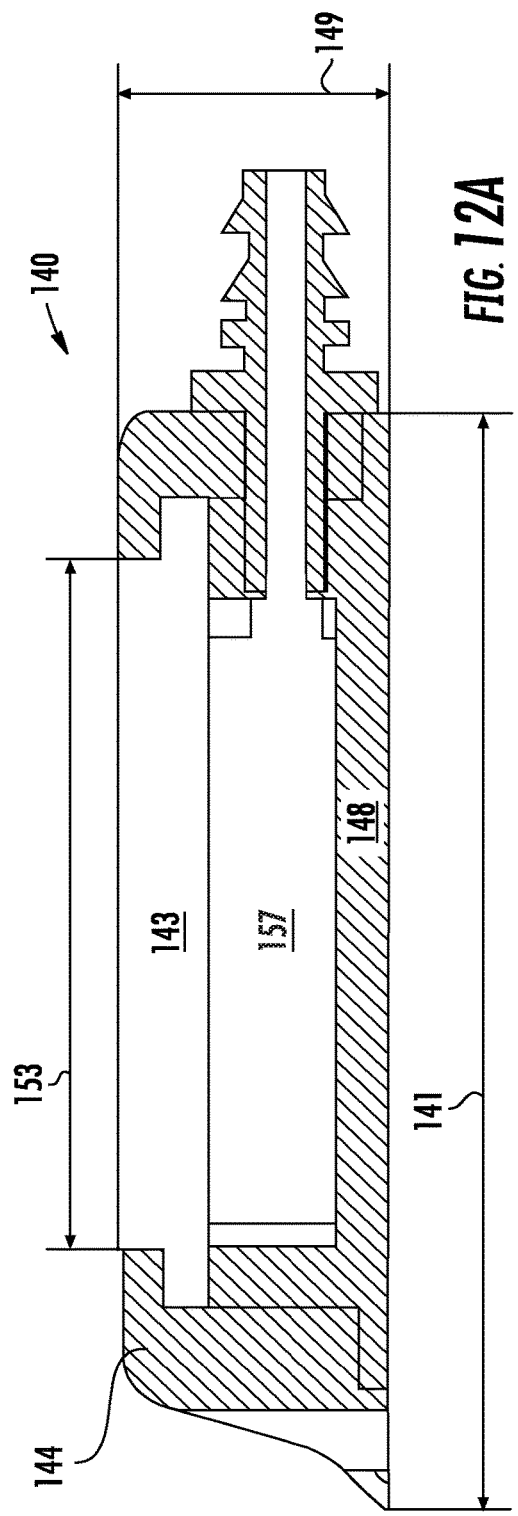
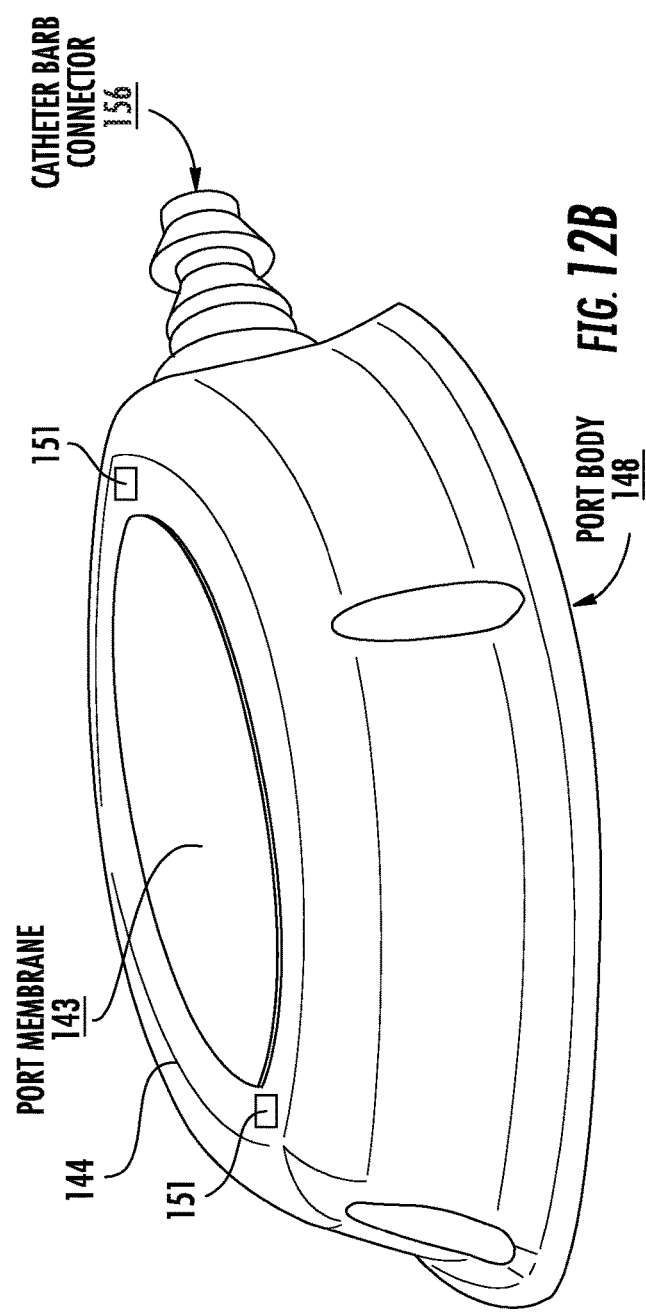

IMPLANTABLE MEDICATION INFUSION PORT WITH PHYSIOLOGIC MONITORING

RELATED APPLICATIONS

The present application is a 371 U.S. national phase application of International Patent Application No. PCT/US2018,033671, filed May 21, 2018, which claims the benefit of U.S. Provisional Application No. 62,509,156, filed May 21, 2017, and U.S. Provisional Patent Application No. 62/573,148, filed Oct. 16, 2017, the disclosures of which are incorporated herein by reference in their entireties.

FIELD OF THE INVENTION

The present invention is directed, generally, to implantable ports used for intravenous medication administration and methods of using the same.

BACKGROUND OF THE INVENTION

Several publications are referenced in this application. The cited references describe the state of the art to which this invention pertains and are hereby incorporated by reference, particularly the systems and methods set forth in the detailed description and figures of each reference.

A port is a device used in the field of medicine for the administration of any intravenous medication, namely chemotherapeutics, but other frequently administered medications and fluids for a plethora of chronic ailments. Similarly, a port device, through its attached catheter, allows for intravenous blood sampling for a variety of laboratory tests. It is a minimally invasive, surgically implanted device, typically placed under the skin of the chest by a physician practicing in the art of surgery, interventional radiology, or other procedural-related fields. Specifically, the device comprises two basic components—a reservoir placed in the subcutaneous tissues (most commonly of the anterior chest wall) and a contiguous tubular catheter member that enters the nearby venous bloodstream. This reservoir is covered with a specialized silicone cap that allows repeated needle access. This requires access by trained personnel with a specialized "non-coring" needle to maintain the integrity of the device, the needle comprising a specialized tip to prevent tearing of the silicone cap or creation of larger holes, limiting the lifespan of the device. The reservoirs and catheters are typically made from biocompatible plastics and/or other polymers and/or metals such as titanium. When implanted, the tubular catheter member typically travels over the clavicle, into the internal jugular vein, and then inferiorly into the superior vena cava where it is intended to terminate near the right atrium. Other, less common, but accepted port placement locations include the subclavian and external jugular veins, and deep veins of the upper arm. Exemplary medication ports currently on the market include the PowerPort®, Medi-Port, Port-A-Cath®, Smart Port, and Bioflo. Most port catheters in practice are of a single-lumen configuration. However, other ports have been designed and used with multiple reservoirs and multiluminal catheter arrangements for the infusion of either simultaneous fluids or for fluids required by the patient's condition known to react or precipitate.

Chemotherapy patients typically have an infusion port placed into the chest via a minor surgical procedure. Ports allow for infusion of chemotherapy and other medications directly into the central venous system (with the catheter tip typically positioned in the superior vena cava or right atrium). Ports also allow for blood draws for routine lab tests. These devices are useful for any patients that require long-term IV medication, nutrition administration, fluid support, or those with difficult vascular access. Ports remain sterile under the skin with no external features.

Implantable ports have many advantages for use in patients that require frequent, repeated administration of intravenous medications. Many medications are known to cause damage to the vein wall of a peripheral vein, including thrombosis, stenosis, overt occlusion, and/or pain. Additionally, because port devices have a catheter with a relatively large lumen resting in the central veins, they offer a means of accurate blood sampling for laboratory testing without a high risk of hemolysis. As a surgically implanted device that resides completely within the body, ports have a lower risk of infection when compared with other indwelling venous catheters such as central venous catheters (CVC), peripherally inserted central catheters (PICC), or others such as subcutaneously tunneled and cuffed catheters seen for long-term vascular access and dialysis. The method of access is also related with lower reported perceived pain when compared with a peripheral phlebotomy or placement of a peripheral IV. For these reasons, ports are the preferred method of vascular access for cancer patients requiring chemotherapy as well as patients with certain additional indications, such as a requirement for long term antibiotic medications in cystic fibrosis, clotting factor replacement and transfusion in hemophilia and other blood dyscrasias, replacement therapy for alpha 1-antitrypsin deficiency, and administration of analgesics for patients with chronic pain, to name only a few exemplary clinical scenarios.

Although longstanding stalwarts in cancer care, and adequate for the stated function, commercially available ports have several limitations. Because they rest under the skin and within the body, they need to be easily identifiable for access. Current models contain a reservoir that is relatively tall and bulky, sometimes with palpable bumps or edges, by purposeful design, causing a visible and palpable bulge under the skin of the chest. When a skilled healthcare worker needs to access the port, the reservoir is first visualized and then palpated deep to the skin. Once the area is sterilized, a non-coring (Huber) type needle is used to access the port through the skin while the substantial device is trapped between the fingers of the accessing medical provider. Heretofore, there has been a clinical need for the port to be visible and palpable, which has required placing the device within the chest wall just inferior to the clavicle. This results in a variable degree of pain or discomfort, cosmetic concerns for the patients, and is a constant reminder of their disease process with associated psychosocial considerations. For these reasons, patients frequently request removal of their port at the earliest possible time, even though it may be recommended to retain their port for additional future venous access.

SUMMARY OF THE INVENTION

One aspect of the invention overcomes shortcomings of current devices by allowing for a lower-profile medication port that is nearly imperceptible by the patient and reduces discomfort.

Another aspect of the invention provides a port that integrates electronic identification and/or localization tools to ensure accurate patient and device identification and/or location. This identification feature also preferably allows linking of all uses of the port to that patient's record for transmission of an accurate record of treatment, for example cancer care. It is believed current ports on the market do not contain any advanced technology beyond those required for vascular access and medication administration. Specifically, there are no means of electronic identification of the device or the patient, or localization of the device. Additionally, it is believed, current ports have no technology that allows for physiologic monitoring of the patient. Given the risks associated with improper patient identification or medication administration as well as the risk of clinical deterioration, applicants have discovered it would be beneficial for an indwelling port to contain advanced electronic identification and monitoring technology with the capability of transmitting data to a server-based computing platform, such as an electronic medical record (EMR).

Another aspect of the invention provides a port and method that allows for advanced physiologic monitoring. It is believed current ports have no means of identification, collection of data, or transmission of information. At most, ports may have some minimal degree of metallic material used simply to make it identifiable by radiography, or with the letters "CT" to identify its ability to withstand pressures of a so-called computed tomography (CT) power injection (typically, defined as infusion rates at a minimum of 5 milliliters per second). Thus far, this most basic data is the only information that can be interpreted from this device once implanted. The simple contemporary ports contain only the hardware required to infuse medication (or other fluids) and withdraw blood. As described herein, it is preferable if a medication port includes embedded identification information about the device, the patient, and the patient's treatment history which could be extracted electronically. According to preferred embodiments, the port monitors orientation and vector acceleration to track patient body orientation, physical activity, exercise, and gait, and to trigger alerts for fall prevention and identification of other characteristically unsafe conditions. This information could advantageously decrease the incidence of errors of patient identification, medication administrations, and care management. Additionally, this information could then be linked to every use of the port so that treatment records and port maintenance could be stored in a local and/or centralized database and in the electronic medical record. Such data could be collected at the facility level, or become portable, such that a patient has the ability to obtain care at more than one facility and maintain a cohesive and complete cancer care record. Finally, such transfer of electronic data could be accessed and managed by the patient for their own understanding and planning. Preferably, the port is optimized to deliver medications at controlled rates or medications of non-traditional types, including stem cell, viral, bacterial, fungal, yeast, protein, DNA, or RNA based agents. For the purposes of medication delivery, a port may be fabricated from permeable or bio-absorbable materials to allow elution of fluid, gaseous, powdered, granulated, or solid form pharmaceutical or biologic agents.

Another aspect of the invention relates to improved medication ports having a low profile, or flattened reservoir compared to current devices on the market. Preferably, the ratio of height or depth of the devices compared to the largest width (e.g., rectangular devices) or diameter (e.g., disc-shape) is less than ⅓, even more preferably, less than ¼ and most preferred less than ⅕. For example, referring to FIG. 2A, the device shown has a lower profile (lower height/width ratio) compared to the taller device in FIG. 1.

Another aspect of the invention relates to a second device, complementary to the medication port system, which is a handheld identification device. This device is preferably used by the healthcare professional or caregiver to locate the port reservoir as the port is preferably not easily visualized or palpated due to its preferred low profile. According to preferred embodiments, the handheld device has detecting electronics that sense the location of the port reservoir in three-dimensional space, as well as extract the information embedded within the electronics within the port (for example, RFID tags), and also includes physiologic sensors, or other data storage devices embedded in the port. Preferred embodiments of the device can also be identified by a characteristic external shape (e.g. oval, square, round), surface texture, protrusion or bump; or in response to a signal, the device may change its motion state, illumination, shape, or configuration of protrusions to indicate device response, change of state, or status. For example, the device may vibrate or self-illuminate when physically tapped or signaled by the handheld device; or it may change dimensional aspect ratio or extend a physical protrusion in response to a signal from the handheld device.

Once the location of the port is identified by the detection system, the handheld device provides instructions to the user for precise localization for needle access and other actions. These instructions may comprise audible, visual, or tactile feedback mechanisms, or any combination thereof. For example, in one embodiment, the handheld device is used to remotely power light emitting diodes (LEDs) on the surface or periphery of the port that transilluminate through the skin. These LEDs can be visualized and aligned with the handheld device for accurate targeting of the port during needle access. The handheld detector may then alert the user when the precise location of the port reservoir is identified. A target, provided by the handheld device, includes any number of visual tools that may be employed to guide the user and the access needle, including, but not limited to, laser or other illuminated cross hairs, physical guides on the handheld device, ink markings, or any other means of showing the user where the center of the reservoir internally rests. The detector is preferred to be a multiuse device that also leaves a space or aperture to prepare the overlying skin in a sterile manner.

According to yet another aspect of the invention, in addition to localizing the port reservoir, the handheld device can preferably also be used as a data-retrieval and data-entry tool that then communicates with the local electronic medical record and/or a centralized, proprietary database that monitors the use of each port. The handheld device preferably has a touch-screen interface that provides an interactive system or means of two-way electronic communication between the user and the system. Preferably, the touch-screen display can assist in the localization and access procedure by displaying instructions for localizing the port, as well as anatomic diagrams showing the port location within the patient. Once the port is identified, information regarding that specific port and the patient will be displayed on the screen. This will allow the user to confirm that the correct patient is in place and the correct port is in use.

Once the port has been accessed, the user can then use the touch-screen interface on the handheld device to enter information regarding the use of the port and/or interventions being performed during that access session. For example, the healthcare professional could enter information such as, "port flush," or "labs drawn for CBC and CMP," or "chemotherapy infusion, cisplatin 100 mg/m$^2$". This information is then transmitted to the electronic medical record (EMR) as well as to a proprietary database that will monitor the use and maintenance of each port. Preferably, communication between the handheld device and the EMR and the database will be through a known means of wireless communication such as wireless broadband communication (Wi-Fi) or Bluetooth.

Preferably, entry of many additional aspects of patient care may be made through this handheld communication device including, but not limited to vital signs, physical exam findings, performance status, lab values, other medication administration such as steroids and antiemetics, adverse chemotherapy reactions, diagnoses including comorbid medical conditions, allergies, and other patient identifiers like face photos and date of birth, amongst many others. Any physiologic data stored by the port device can also be extracted by the handheld device and transmitted to the database and to the EMR. The handheld device described herein can be a custom designed device or an off-the-shelf smart device such as a smart phone or tablet computer with custom and proprietary software applications to perform the functions described herein. Additionally, the port device itself could contain hardware and software required for direct WiFi, Bluetooth, or cellular communication, not requiring the use of a handheld device.

According to preferred embodiments, data collected from the port and the handheld device is communicated to the EMR for record keeping in the clinic or hospital where therapy is delivered. That data is simultaneously stored in a proprietary and secure database, offsite. Information in this database is preferably used to track a patient's therapy as well as port maintenance. This information is preferably accessible by that patient as well as the patient's healthcare team. Through this database, the patient and their healthcare providers can preferably be alerted when the port needs to be flushed and/or locked with fluids to prevent thrombus, or when the patient is due to have labs drawn or medication administered. Additionally, the database will preferably keep an accurate record of every use of the port, which essentially provides a detailed record of that patient's therapy, giving each patient ownership of an accurate, individualized, and portable summary of their cancer care. All storing of information and communication is preferably compliant with the Health Insurance Portability and Accountability Act of 1996 (HIPAA) and the system and/or methods will preferably utilize data security software and hardware known in the art to prevent external hacking or other malicious uses of patient data. Communication with the electronic medical record may require use of a third-party interface that is HIPAA compliant. The port and/or hand-held device may also utilize redacting software protocols to exclude certain private patient information to enable data transmission by non-HIPAA compliant software, servers, and networks.

As the amount of stored treatment and physiologic data increases, database analytics will be applied in a way that will allow for decreased treatment related complications and improved outcomes. Machine learning, artificial intelligence, and augmented intelligence can be applied to the incoming monitoring data to predict patients who are declining clinically or who are at risk of a major illness and hospitalization. These algorithms can alert the patients, their families, and their care teams and early interventions can be implemented with the aim of preventing complications and unnecessary hospitalizations. These analytics can be paired with a mobile or web-based application that allows patients to also enter subjective data about how they feel or symptoms they are experiencing.

Within this database, data will also preferably be anonymized for use in analysis and evaluation regarding patterns of cancer care, adverse reactions, treatment efficacy and other outcomes based or comparative effectiveness research. With enough ports in use, the database will provide a representative cross section of cancer care throughout the country (and perhaps the world) and will give critical information regarding outcomes of specific diseases, use of specific therapeutics, access to care, and adverse outcomes. This information will be useful to government organizations tasked with developing healthcare policy and regulating pharmaceuticals and medical devices, academics performing cancer and rare disease research, pharmaceutical companies evaluating the use of their and their competitors' products, marketing organizations involved in selling therapeutics, and financial organizations tasked with investing in medical companies and allocating capital to emerging technologies.

The foregoing has outlined some of the aspects of the present invention. These aspects should be construed strictly as illustrative of some of the more prominent features and applications of the invention, rather than as limitations on the invention. Many other beneficial results can be obtained by modifying the embodiments within the scope of the invention. Accordingly, for other objects and a full understanding of the invention, refer to the summary of the invention, the detailed description describing the preferred embodiment in addition to the scope of the invention defined by the claims and the accompanying drawings. The unique features characteristic of this invention and operation will be understood more easily with the description and drawings. It is to be understood that the drawings are for illustration and description only and do not define the limits of the invention.

BRIEF DESCRIPTION OF THE DRAWINGS

The above-mentioned and other features of the inventions disclosed herein are described below with reference to the drawings of the preferred embodiments. The illustrated embodiments are intended to illustrate, but not to limit, the inventions. The drawings contain the following figures:

FIG. 12A is a side schematic cross-sectional depiction of an ellipsoid implantable port device according to another embodiment of the invention. FIG. 12B is a side perspective top view depiction of the device of FIG. 12A.

DETAILED DESCRIPTION OF THE INVENTION

The present invention will now be described in detail hereinafter by reference to the accompanying drawings. The invention is not intended to be limited to the embodiments described; rather, this detailed description is provided to enable any person skilled in the art to make and practice the invention.

One aspect of the invention relates to implantable port devices having low profiles to reduce the patient's discomfort and visibility. Preferably, a low profile implantable medication port that is nearly imperceptible by the patient or others and can be localized electronically despite its low profile.

Current ports are identified and located via palpation of the patient chest region by the medical professional. That is, implant access is obtained by locating the port under the skin of the patient's chest and inserting a non-coring needle through the silicon diaphragm and into the port reservoir.

In order to ensure localization via palpation, current ports have a tall profile that causes protrusion of the skin of the chest. This protrusion causes discomfort for patients, is a constant reminder of their cancer or other medical problems, and is not cosmetically appealing.

Figure 1:
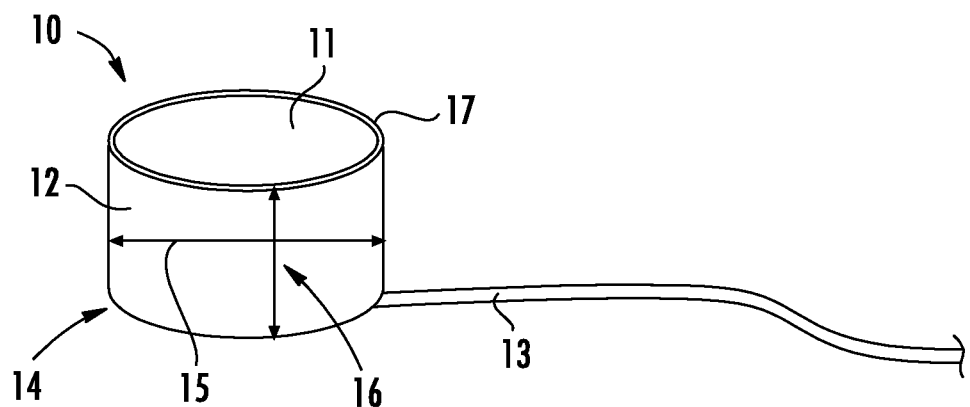
FIG. 1 is a side perspective top view depiction of one implantable port.
Figure 2A:
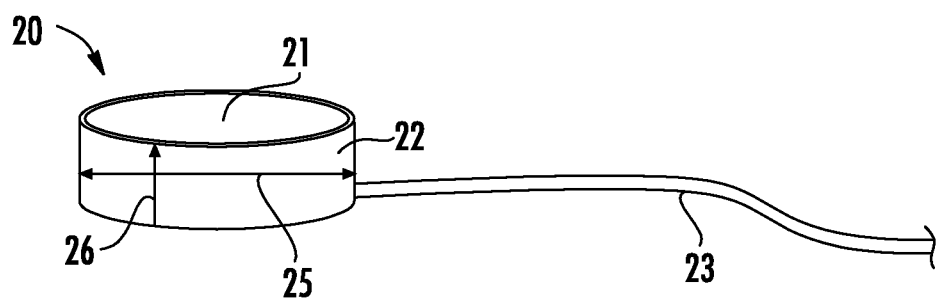
FIG. 2A is a side perspective top view depiction of a low profile implantable port device according to one embodiment of the invention.

Comparing the implant device 10 in FIG. 1 and device 20 in 2A, the device 20 shown in FIG. 2A has a lower profile allowing the implant device to have a lower visible profile in the patient reducing discomfort and other complications. According to the invention, the implant devices are designed to have a lower profile while still providing at least one reservoir within the cavity of the device (e.g., by using round disc-like shapes, thinner housing components, improved configuration and/or design, etc.). Moreover, according to preferred embodiments, the low profile devices include electronics allowing the implanted devices to be located despite having a low profile.

Preferably, the reservoir comprises a housing made from biocompatible plastic or other polymer, an MRI safe metal such as titanium, or some combination thereof, but is preferably sufficiently rigid on its deep/posterior and lateral portions thereof, and, preferably, cannot be punctured by a medical needle. The posterior and lateral rigidity may also be achieved in a flexible, conformable reservoir with a honeycomb or lattice internal structure.

The reservoir preferably further comprises a cap disposed at the superficial/anterior margin that can easily withstand multiple needle accesses and have self-sealing properties. This cap is preferably made from silicone or a similar deformable, self-sealing, biocompatible material. The reservoir preferably is only sufficiently tall for receipt of a port access needle, but has a low enough profile as to be nearly imperceptible by the patient or others when implanted under the skin and subcutaneous tissues. It is envisioned that the reservoir will be round and generally shaped like a disc, but it is within the scope of this invention for the reservoir to take any shape that allows proper function.

One embodiment relates to a medical implantable port device adapted for intravenous medication administration, the device comprising:
 (a) a housing made of a biocompatible material and having an aspect ratio (i.e., width/height ratio) greater than 3/1, more preferably greater than 4/1, even more preferably greater than 5/1, even more preferably greater than 6/1;
 (b) a first fluid cavity enclosed by the housing; and
 (c) a cap forming the top of the housing and made of self-sealing, biocompatible material.

Preferably, the devices are adapted by its shape, size, weight, materials used, components included, and/or the configuration of the device components.

Another embodiment relates to a medical implantable device for intravascular medication administration, the device comprising: a) a non-collapsible housing of diameter or width to thickness ratio of 3 or greater; b) a first fluid cavity enclosed by said housing; and c) a cap forming the top of said housing and made of self-sealing material.

Preferably, the diameter or width to thickness ratio of 3 or greater, but less than 50.

According to preferred embodiments, a non-collapsible housing designed, configured and/or adapted to be capable of withstanding the negative pressures applied when aspirating blood through the device. This may be achieved by selecting the materials (e.g., type of plastic material(s) used), design (e.g., dimensions including thickness), configuration (e.g., use of support structures) and/or method of making (e.g., injection molding vs other methods).

According to alternative embodiments, the ratio is less than 3 and greater than 2.

According to preferred embodiments, the ratio is greater than 3.5, more preferably greater than 4, and even more preferably greater than 4.5.

Preferably, the device further comprises at least one catheter in fluid communication with the first fluid cavity.

Figure 2B:
FIG. 2B is a bottom view depiction of the inventive port device shown in FIG. 2A.

Referring to FIG. 2A and FIG. 2B, the components of the port device 20 include a rigid reservoir housing 22 comprised of biocompatible plastic, metal, or other material that provides rigidity and strength to prevent needle puncture. The reservoir housing 22 preferably is short in stature, or low-profile, as to make it nearly unnoticeable to and/or more comfortable for the patient. The reservoir housing 22 is hollow, providing at least one reservoir therein for holding pharmaceuticals or drugs or related materials to be flushed forward into the central venous system. The reservoir (not shown) is covered by a cap or diaphragm 21 that allows receipt of an access needle or catheter (not shown in FIGS. 2A and 2B). This cap 21 is preferably made from silicone or a similar self-sealing material that allows for multiple needle access procedures. Preferably, in fluid communication with the reservoir is an attached catheter 23. Once inserted surgically, the catheter tip rests in a central venous structure such as the superior vena cava or right atrium and is in fluid communication with the central venous blood. The reservoir and catheter may contain valves or other mechanical structures to prevent blood accumulation, thrombus, or biofilm accumulation and possible resultant bacterial contamination.

According to preferred embodiments, the aspect ratio or width/height ratio of the device 20 is greater than 3.0, more preferably greater than 4.0, even more preferably greater than 5.0 and most preferred greater than 6. Preferably, "aspect ratio" as used herein is defined as width/height (unless stated otherwise). Referring to FIG. 2A, the width is shown as line arrow 25, while height shown by line arrow 26. In contrast, FIG. 1 shows a device having an aspect ratio or width/height ratio less than 3.0 and closer to 2 as shown by width 15 and height 16 resulting in a "taller" port that would be more uncomfortable to the patient and more visible.

Preferably, the device 20 has a height (26) less than 0.5 inches, more preferably less than 0.4 inches even more preferably less than 0.35 inches and most preferred less than 0.3 inches.

Preferably, the biocompatible material used for the housing components is rigid compared to the self-sealing, biocompatible material used the membrane. Preferably, the housing components 22 are made of plastic materials sufficiently rigid to maintain the device shape after implanting and while a needle is pushed through the membrane. Suitable plastic materials include polycarbonate and related materials. Alternatively, the housing components 22 comprise metal materials such as titanium.

Preferably, the device further includes at least one catheter 23 in fluid communication with the first fluid cavity and a vein, artery, or heart chamber. The catheter connector (not shown in FIG. 2A) is adapted to attach a catheter 23 as described, for example, in FIGS. 10A and 10B (catheter barb connector 106), FIGS. 11A and 11B (catheter barb connector 126), and FIGS. 12A and 12B (catheter barb connector 156).

Figure 3A:
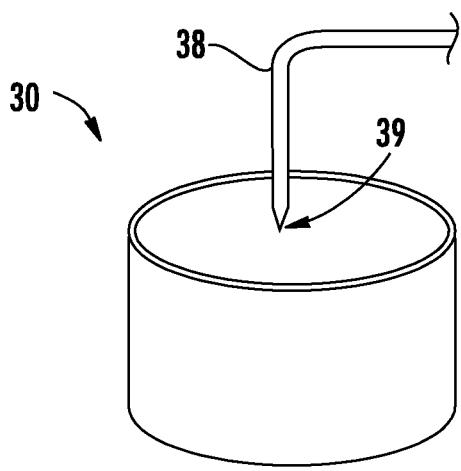
FIG. 3A is a side view of an implantable port device showing access of the port reservoir with a non-coring (Huber) type angled needle located above the port for insertion.
Figure 5:
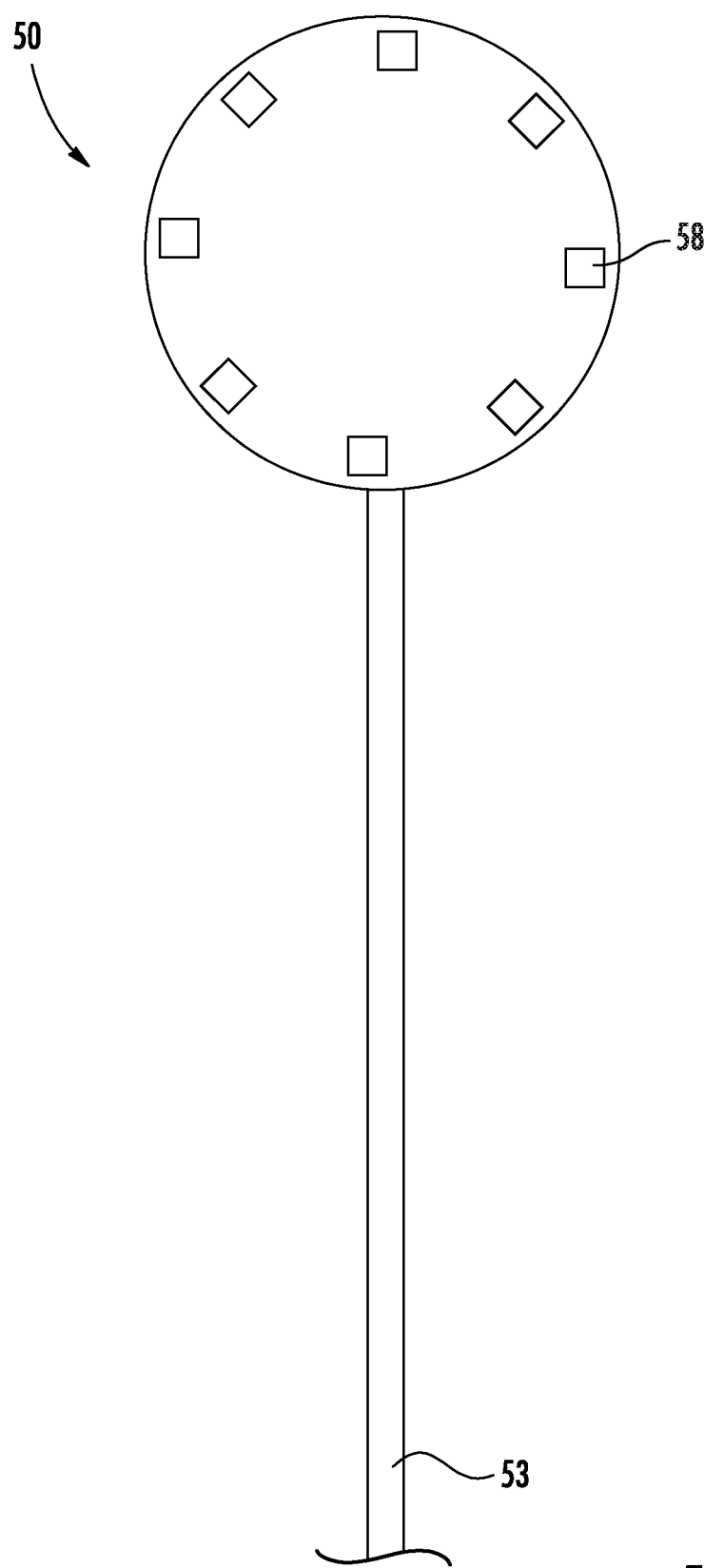
FIG. 5 is a bottom view of an implant device showing an alternative embodiment of a multichip array according to another embodiment of the invention.

Preferably, the device further includes at least one catheter in fluid communication with the first fluid cavity, for example, catheter (13) in FIG. 1, catheter (23) in FIGS. 2A and 2B, catheter 38 in FIG. 3A, and catheter (53) in FIG. 5.

Moreover, it is believed current ports on the market do not contain any advanced technology beyond those required for vascular access and medication administration. Specifically, there are no means of electronic identification of the device or the patient, or localization of the device. Additionally, it is believed, current ports have no technology that allows for physiologic monitoring of the patient. Given the risks associated with improper patient identification or medication administration as well as the risk of clinical deterioration, applicants have discovered it would be beneficial for an indwelling port to contain advanced electronic identification and monitoring technology with the capability of transmitting data to a server-based computing platform, such as an electronic medical record (EMR).

According to preferred embodiments, the device further comprises at least one identifier associated with the first fluid cavity by communication or contact. Preferably, the identifier is defined by electromagnetic, acoustic, mechanical, or optical devices or means. Preferably, the communication defined by electromagnetic signal, acoustic signal, mechanical movement, or optical signal. Preferably, the contact being direct or indirect electromagnetic, acoustic, physical, or optical.

According to preferred embodiments, the device further comprises at least one data storage device.

According to preferred embodiments, the device the at least one identifier comprises radio-frequency identification, microwave frequency identification, magnetic identification, sound frequency identification, mechanical vibratory identification, mechanical feature identification, light color, or light wavelength identification.

According to preferred embodiments, the at least one identifier is an element of an array of identifiers.

According to preferred embodiments, the at least one electronic identifier comprises a centrally located radio-frequency identification (RFID) tag.

According to particularly preferred embodiments, the at least one identifier is capable of remote activation.

According to preferred embodiments, the intravascular medication administration is achieved through an attachable or pre-connected catheter.

Preferably, blood sampling or interrogation capability is achieved by vascular access catheter, optical fiber, wire, tubule, wicking paper, or wicking fiber.

According to preferred embodiments, the optical fiber is attachable or pre-connected to said device as a single fiber, a fiber pair, or a fiber bundle.

Preferably, the optical fiber, or fibers, are used to enable light transmission and reception.

Preferably, the wire is adapted and/or configured to be attachable or pre-connected to said device as a single wire, wire pair, or wire bundle.

Preferably, the wire is adapted and/or configured to enable impedance, voltage, current, or magnetic field sensing capability.

According to preferred embodiments, the device further comprises one or more electronic devices or sensors. For example, electronic device or sensor (24) shown in FIG. 2B at the center of the device 20 for identification and localization.

Preferably, within or attached to the reservoir, but preferably not in fluid communication with the blood stream, is an electronic identifier and data storage device. Preferably, device will comprise one or more radio-frequency identification (RFID) tag(s). Using an appropriately designed electronic detector (e.g., handheld device), RFID tags can be easily located with a high degree of precision. RFID tags can also carry information about the device and the patient. The identifier port device preferably comprises a single, centrally located RFID tag, and/or an RFID array utilizing multiple tags.

The aforementioned RFID tags could be either "passive" RFID tags that require remote activation and power, or "active" RFID tags. Active RFID tags would require a power source to be imbedded within the device, preferably in the form of a long-lasting battery capable of remote or inductive recharging. In conjunction with the RFID tags and/or a battery, the port preferably includes additional physical and electronic sensors or detectors that can measure, store, analyze, and transmit physiologic data about the patient. These additional sensors may identify, monitor, and communicate patient information by electromagnetic, acoustic, motion, optical, thermal, or biochemical devices or means. Electromagnetic devices or means include impedance, voltage, current, or magnetic field sensing capability with a wire, wires, wire bundle, magnetic node, or array of nodes. Acoustic devices or acoustic means include sound frequency, within human auditory range or below or above frequencies of human auditory range, beat or pulse pattern, tonal pitch melody or song. Motion devices or means include vibration, movement pulse, pattern or rhythm of movement, intensity of movement, or speed of movement. Motion communication may occur by a recognizable response to a signal. This response may be by vibration, pulse, movement pattern, direction, acceleration, or rate of movement. Motion communication may also be by lack of response, in which case a physical signal, vibration, or bump to the environment yields a motion response in the surrounding tissue that can be distinguished from the motion response of the device. Motion communication may also be by characteristic input signal and responding resonance. Optical devices or means include illuminating light wavelength, light intensity, on/off light pulse frequency, on/off light pulse pattern, passive glow or active glow when illuminated with special light such as UV or "black light", or display of recognizable shapes or characters. It also includes characterization by spectroscopy, interferometry, response to infrared illumination, or optical coherence tomography. Thermal devices or means include distinction of device temperature relative to surrounding environment, temperature of device, temperature of environment surrounding device, or differential rate of device temperature change relative to surroundings when device environment is heated or cooled by external means. Biochemical devices or means include use of catheter, tubule, wicking paper, or wicking fiber to enable micro-fluidic transport of bodily fluid for sensing of protein, RNA, DNA, antigen, or virus with a micro-array chip.

In general, these additional sensors can be located within the port housing, on the external surface of the port housing, on the internal surface of the port housing, or on or within the catheter portion or within an enclosed space within the housing. This physiologic data includes but is not limited to temperature, pressure sensors for arterial blood pressure or central venous pressure monitoring, pulse oximetry, pH sensors to detect alterations in acid/base balances, heart rate monitors, heart rhythm, electrocardiogram (ECG) tracings, respiratory rate monitors, body fat percentage, accelerometers to detect activity levels, body movement, falls, gait analysis, and seizure activity, blood glucose monitors, detectors for measuring complete blood counts (hemoglobin or hematocrit, white blood cell levels with differential, and platelets), blood chemistry monitors (sodium, potassium, chloride, bicarbonate, creatinine, blood urea nitrogen, calcium, magnesium, phosphorus, liver function tests such as AST, ALT, alkaline phosphatase, gamma glutamyl transferase, troponin), coagulation studies such as prothrombin time (PT), partial throboplastin time (PTT), and international normalized ratio (INR), drug/medication levels, blood gasses such as partial pressures of oxygen and carbon dioxide, lactate levels, circulating tumor cells, circulating tumor DNA, circulating RNA, hormone levels such as cortisol, thyroid hormone (T4, T3, free T4, free T3), TSH, ACTH, parathyroid hormone, and tumor markers (PSA, beta-HCG, AFP, LDH, CA 125, CA 19-9, CEA, etc.), multigene sequencing of germ line or tumor DNA, markers of inflammation such as cytokines, C reactive protein, erythrocyte sedimentation rate, amongst others known or yet unknown in medicine.

Another embodiment of the invention relates to a medical implantable device for intravascular medication administration and patient monitoring, said device comprising: a) a non-collapsible housing of diameter or width to thickness ratio of 3 or greater; b) a first fluid cavity enclosed by said housing; and c) a cap forming the top of said housing and made of self-sealing material; d) at least one catheter in fluid communication with the first fluid cavity.

Preferably, the ratio is greater than 3.5, more preferably greater than 4.0, and even more preferably greater than 4.5.

According to alternative embodiments, the ratio is less than 3 and greater than 2.

According to preferred embodiments, the device comprises at least one identifier associated with the first fluid cavity by communication or contact.

Preferably, the at least one identifier is an element of an array of identifiers.

Preferably, the at least one identifier is capable of remote activation.

Preferably, the at least one identifier is defined by electromagnetics, by acoustics, by physical feature, by characteristic motion, by optically, and/or thermally.

Preferably, the communication is by passive or active signal or response, by electromagnetic means, by acoustic means, by change in physical feature, by characteristic motion, by optical means, and/or by thermal means.

Preferably, the contact is either direct or indirect, by electromagnetic means, by acoustic means, by physical means, by motile means, by optical means, and/or by thermal means.

Preferably, the device further comprises at least one data storage device.

According to preferred embodiments, the device further comprises physiologic condition sensing capability. Preferably, the physiologic condition sensed is heart rate, blood pressure, blood oxygenation, carbon dioxide concentration, blood sugar, INR level, temperature, fat composition, blood salinity, pH (e.g., of blood, serum, medicine), creatinine level, body orientation, change in body orientation, change in body position, and/or vector acceleration of body.

According to preferred embodiments, the device further comprises one or more electronic components configured to (i) transmit or allow data transmission from the device to an external computer system, (ii) transmit or allow localization data to the external computer system; or (iii) both (i) and (ii).

Preferably, the external computer system includes a handheld device.

Preferably, the intravascular medication administration is achieved through an attachable or pre-connected catheter.

Preferably, the blood sampling or interrogation capability is achieved by vascular access catheter, optical fiber, wire, tubule, wicking paper, or wicking fiber.

Preferably, the optical fiber is attachable or pre-connected to said device as a single fiber, a fiber pair, or a fiber bundle. Preferably, the optical fiber, or fibers, are used to enable light transmission and reception.

Preferably, the wire is attachable or pre-connected to said device as a single wire, wire pair, or wire bundle. According to preferred embodiments, the wire is to enable impedance, voltage, current, or magnetic field sensing capability.

Preferably, the tubule, wicking paper, or wicking fiber enable micro-fluidic transport of bodily fluid. Preferably, the fluidic transport is to enable for bodily fluid chemistry sensing.

Preferably, the blood sampling is to enable sensing of protein, RNA, DNA, antigen, or virus with a micro-array chip.

According to preferred embodiments, the device is equipped with an audio, visual, or vibrational alert to signal device wearer, caregiver of wearer, or emergency responder personnel. Preferably, the alert is related to said fluid cavity by function or status. Preferably, the alert is related to blood sampling result or status.

Another embodiment relates to a medical implantable device for intravascular medication administration and patient monitoring, said device comprising: a) a non-collapsible housing of diameter or width to thickness ratio of 3 or greater; b) a first fluid cavity enclosed by said housing; and c) a cap forming the top of said housing and made of self-sealing material; d) at least one catheter in fluid communication with the first fluid cavity; e) at least one identifier associated with the first fluid cavity by communication or contact; f) at least one identifier capable of remote activation.

Preferably, the ratio is greater than 3.5, more preferably greater than 4.0, and even more preferably greater than 4.5.

Alternatively, the ratio is less than 3 and greater than 2.

Figure 17:
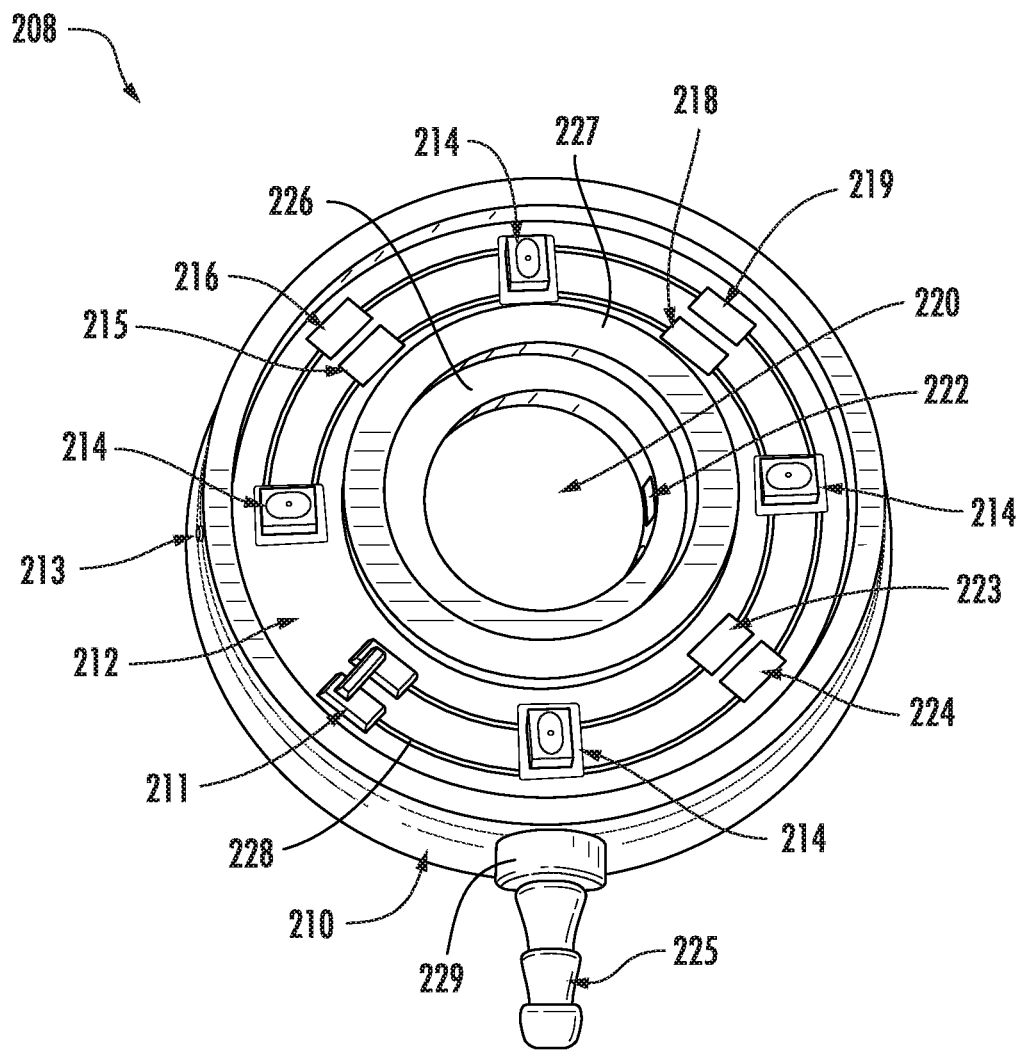
FIG. 17 is a top view of an implant device without a port membrane or cover showing a circular arrangement of inner electronic components according to another embodiment of the invention.

FIG. 17 shows a top view of an implant device 208 according to another embodiment of the invention without a port membrane or cover showing the interior electronic components arranged around the port reservoir 220. Implant device 208 comprises external housing 210 comprising port reservoir 220 enclosed therein and further includes LED devices 214, respiratory rate sensor 218, temperature sensor 219, heart rhythm sensor 223, heart rate sensor 224, accelerometer/activity sensor 216, and pulse oximetry sensor 215; the electronic components are advantageously arranged around port reservoir 220. Blood pressure sensor 222 is shown within the port reservoir 220. Implant device 208 further includes near field communication chip 211 adapted to transmit information and data to and from the implant device 208. Implant device 208 includes circular electric leads 228 on a disk-shaped circuit board 212 for connecting the electronic components to a power source (not shown). This circular configuration around port reservoir 220 allows for many LEDs and other electronic devices to be arranged within implant device 208. Housing 210 includes a circular top surface supporting disk shaped circuit board 212 with circular leads 228. Housing 210 further includes an opening (not shown) fluidly connecting catheter barb connector 225 (having connector base 229) with port reservoir 220. Port reservoir 220 includes a lower circular ridge surface 226 and an upper circular ridge surface 227 (ridges 226 and 227 are adapted for fitting, for example, a silicone membrane onto the top of the housing). Housing 210 further comprises at least one suture fixation hole configured to allow implant device 208 to be secured within the chest wall of a patient (not shown).

Figure 18:
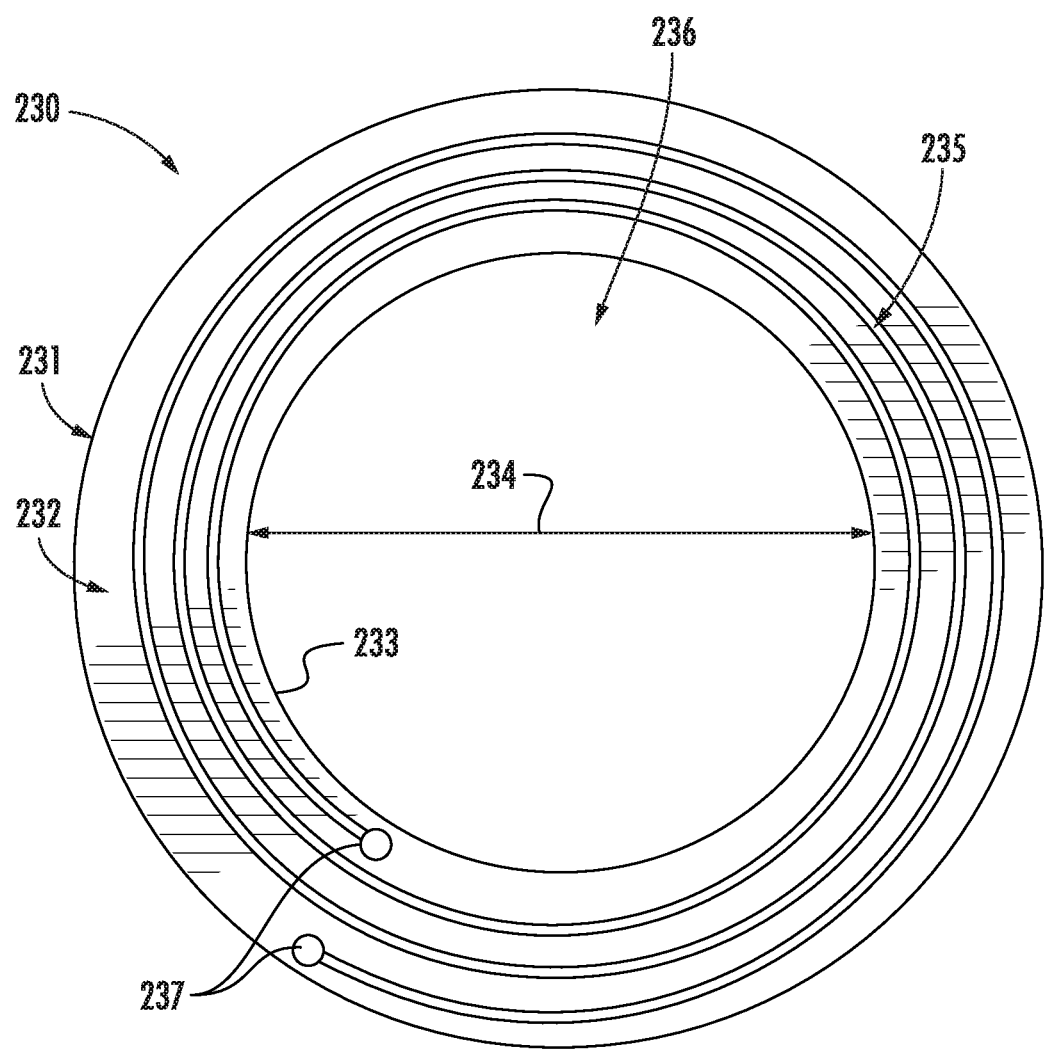
FIG. 18 is a bottom view of a circuit board for use with an implant device according to another embodiment of the invention.

FIG. 18 shows disk-shaped circuit board 230 configured and/or adapted for use with an implant device (not shown) according to another embodiment. Circuit board 230 has a surface 232 comprising circular electric leads 235 terminating at contacts 237. Disk-shaped circuit board 230 is configured to surround and provide an opening 236 for accessing a port reservoir, for example as shown in FIG. 17. Circuit board 230 has an outer circumference 231 and inner circumference 233, with the circular electric leads 228 disposed on surface 232 in between.

The outer diameter of disk-shaped circuit board 230 preferably ranges from 0.25 to 3 inches, more preferably 0.5 to 2 inches, even more preferably 0.75 to 1.5 inches and most preferred 1.0-1.25 inches. The diameter 234 of opening 236 preferably ranges from 0.25 to 1.5 inches, even more preferably from 0.5-1.0 inches and most preferably from 0.65-0.85 inches. The thickness of disk-shaped circuit board 230 (difference between outer circumference 231 and inner circumference 233) preferably ranges from 0.1 to 1 inch, even more preferably from 0.2 to 0.75 inches, and most preferred from 0.25 to 0.5 inches.

Preferably, the device comprises at least one electronic identifier (a) within the first fluid cavity or in contact with the first fluid cavity or (b) on an outer surface of port reservoir or device or (c) within the device housing, but not in contact with first fluid cavity.

Preferably, the device comprises at least one data storage device. For example, at least one data storage device to store identification information about the device and/or the patient, to track dosage, body temperature, heart rate, blood pressure, patient activity and/or any other data. This data storage device may be a readable and/or writable data storage chip, electronic hardware component, or device used to store history of device use and status, collected patient data, or data downloaded from an external source.

Preferably, the device comprises at least one electronic identifier comprising one or more radio-frequency identification (RFID) tag(s).

Preferably, the device comprises at least one electronic identifier comprising an array of radio-frequency identification (RFID) tag(s). For example, the circular array of radio-frequency identification (RFID) tags (58) shown in FIG. 5.

Preferably, the device comprises at least one electronic identifier comprising a centrally located radio-frequency identification (RFID) tag, as shown, for example, as tag 24 in FIG. 2B.

Figure 11A:
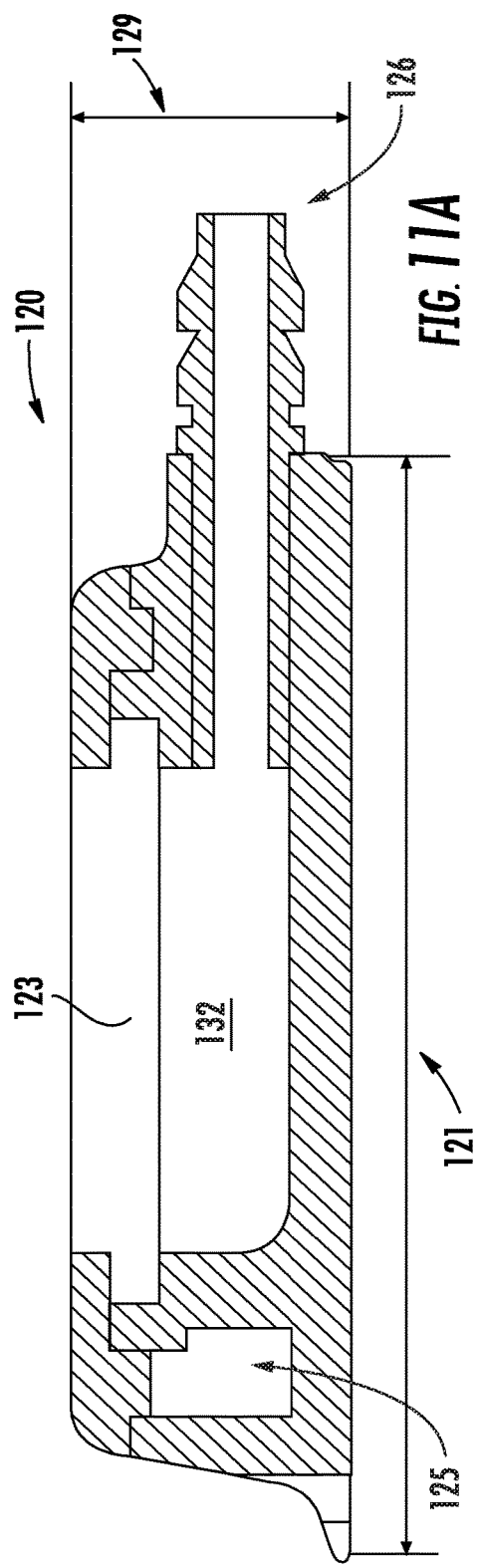
FIG. 11A is a side schematic cross-sectional depiction of a disc-shaped implantable port device according to another embodiment of the invention.
Figure 11B:
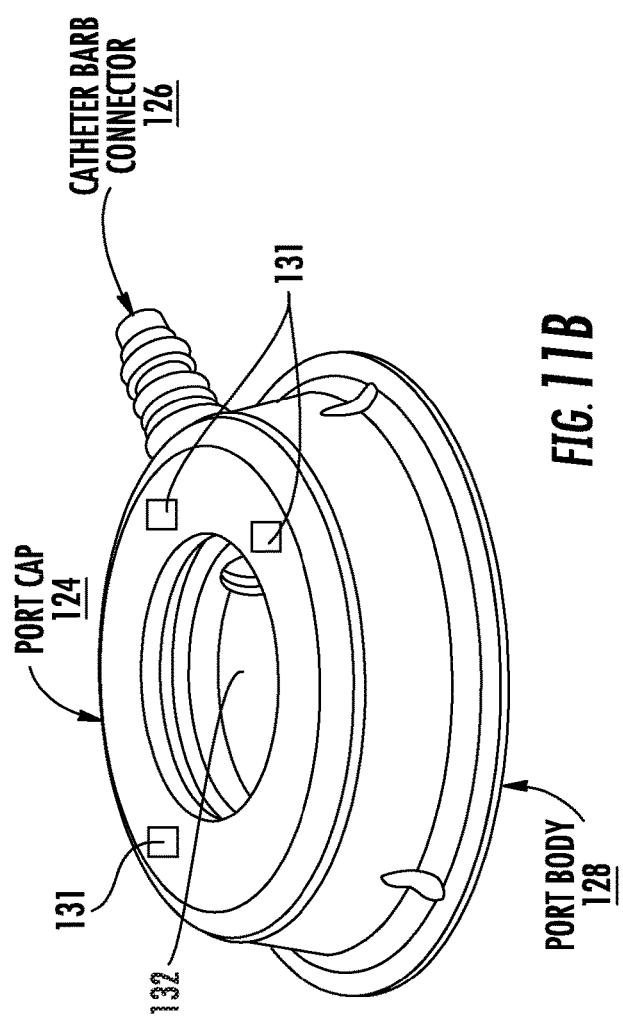
FIG. 11B is a side perspective top view depiction of the device of FIG. 11A.

According to additional preferred embodiments, the device includes one or more lights or light emitting diodes (e.g., LEDs) or other light emitting devices adapted and/or configured to emit light through the patient's skin when the device is implanted, for example LEDs 131 in FIG. 11B, and LEDs 151 in FIG. 12B. The lights are adapted and/or configured (e.g., by location, size, intensity, power, alignment, etc.) to allow for localization of the device and, preferably, it's orientation, either visually or using a handheld device.

Preferably, the device comprises one or more lights capable of remote activation. For example, one or more LED lights on the top surface of the implanted device that can be activated by a medical provider or caregiver (e.g., using a handheld device) to emit lights so that the implanted device's location and orientation can be determined by the medical provider or caregiver.

Preferably, the device comprises an array of two or more lights capable of remote activation. Preferably, the array of lights is configured to improved localization and orientation determination. For example, the circular array of LEDs (58) shown in FIG. 5.

Preferably, the device comprises an array of two or more LEDs capable of remote activation.

Preferably, the device is adapted to extract a sampling of venous blood from a patient with the device for testing. For example, blood can be aspirated through the needle or catheter used for port access and infusion, or alternatively the device comprises a second catheter port for connecting a sampling catheter for extracting fluids or one or more flow cells within the device.

Another embodiment of the relates to the port device described herein and further comprising a tubule, wicking paper, or wicking fiber adapted or configured to enable micro-fluidic transport of bodily fluid. Preferably, the fluidic transport is to enable for bodily fluid chemistry sensing. Preferably, blood sampling is to enable sensing of blood counts, blood and body chemistry, protein, RNA, DNA, antigen, or virus with a micro-array chip.

The implantable device of the invention may have a variety of shapes, but preferably has a low profile. Preferably, the housing has the shape of a disc having a height ranging from 0.25 to 0.35 inches, or preferably less than 0.25 inches, and a diameter ranging from 1.0 to 1.5 inches, or preferably less than 1.0 inches. See, for example, the variety of shapes shown in FIGS. 1-5 and FIG. 11.

FIGS. 11A-11B shows a disc-shaped implant device including implant port device body 128, port cap 124, port membrane 123 (not shown in FIG. 11B) and a reservoir 132 (within device body 128 and below port membrane 123) fluidly connected to catheter barb connector 126. Inner space 125 preferably includes one or more sensors or other electronics (not shown). FIG. 11A shows a device having a height 129 (for example, 0.285 inches) and a largest width dimension 121 (for example, 1.127 inches) providing a low profile, according to one embodiment of the invention.

Figure 16:
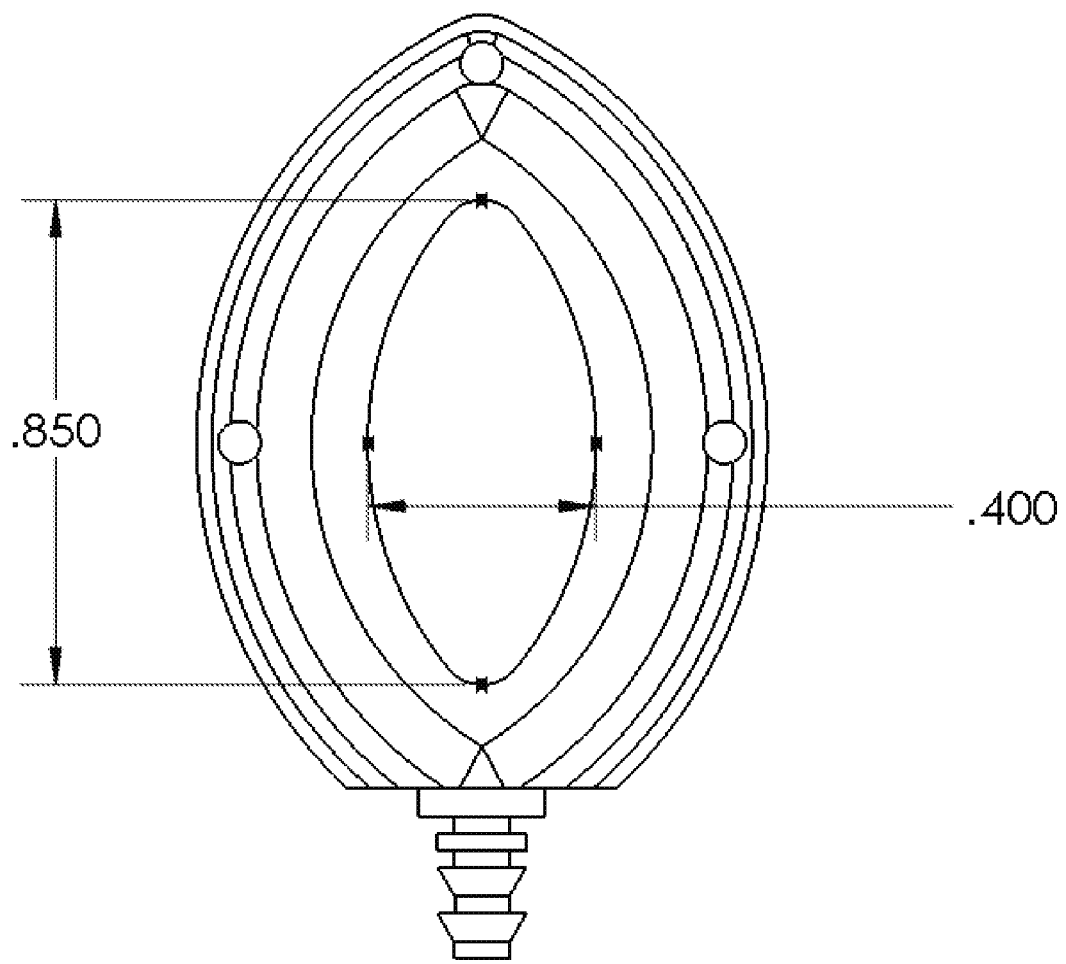
FIG. 16 is a top schematic view of the device of FIGS. 12A and 12B.

According to alternative embodiments, the housing has the shape of an oval. See, for example, FIGS. 12A, 12B and 16. Preferably the housing has the shape of an oval having a height ranging from 0.25 to 0.35 inches, a smallest width ranging from 0.5 to 1.5 inches and a largest dimension or length ranging from 1 to 3 inches. For example, for an oval shaped device, the reservoir would also preferably have an oval shape and preferably has as width ranging from 0.25-1.00 inch, preferably 0.30-0.75 inches and most preferred 0.4 to 0.5 inches and a length ranging from 0.4-2.00 inches, more preferably 0.5-1.5 inches, even more preferably 0.75 to 1.00 inches. See, for example, the dimensions shown in FIG. 16.

FIGS. 12A-12B shows an oval-shaped implant device including implant port device body 148, port cap 144, port membrane 143 (sealing opening 153) and a reservoir 157 fluidly connected to catheter barb connector 156. FIG. 12A shows a device having a height 149 (for example, 0.330 inches) and a largest width dimension 141 (for example 1.356 inches) providing a low profile, according to one embodiment of the invention.

Figure 10A:
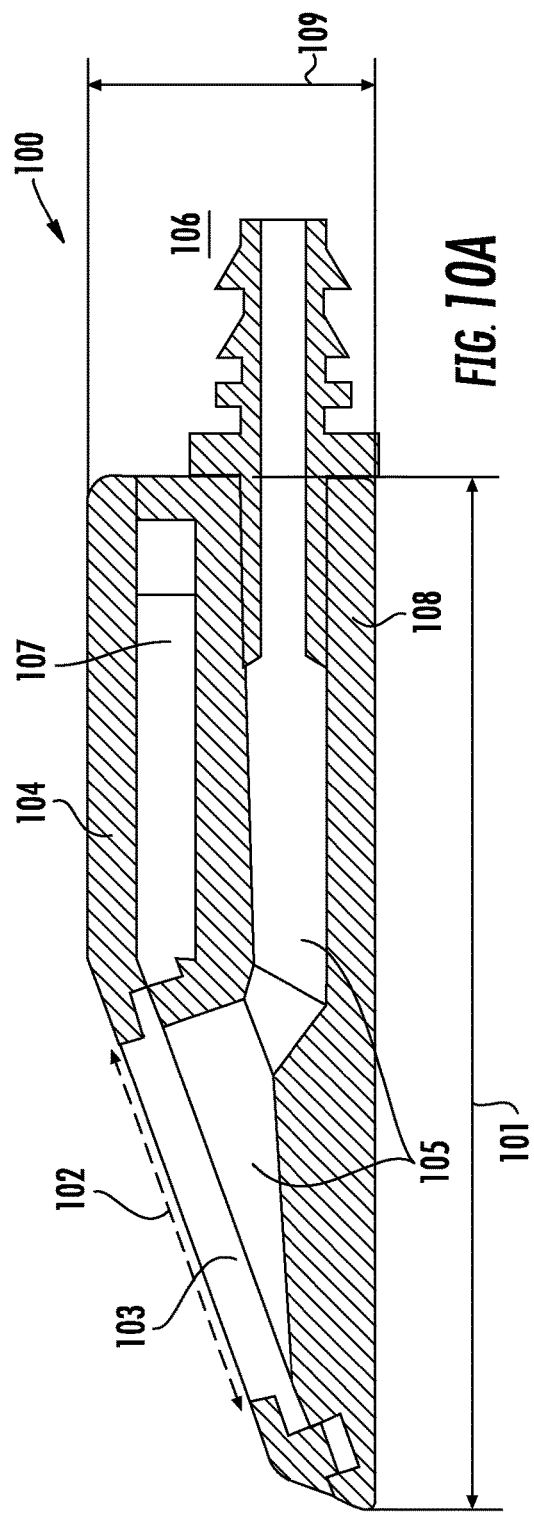
FIG. 10A is a side schematic cross-sectional depiction of an implantable port device according to another embodiment of the invention.
Figure 10B:
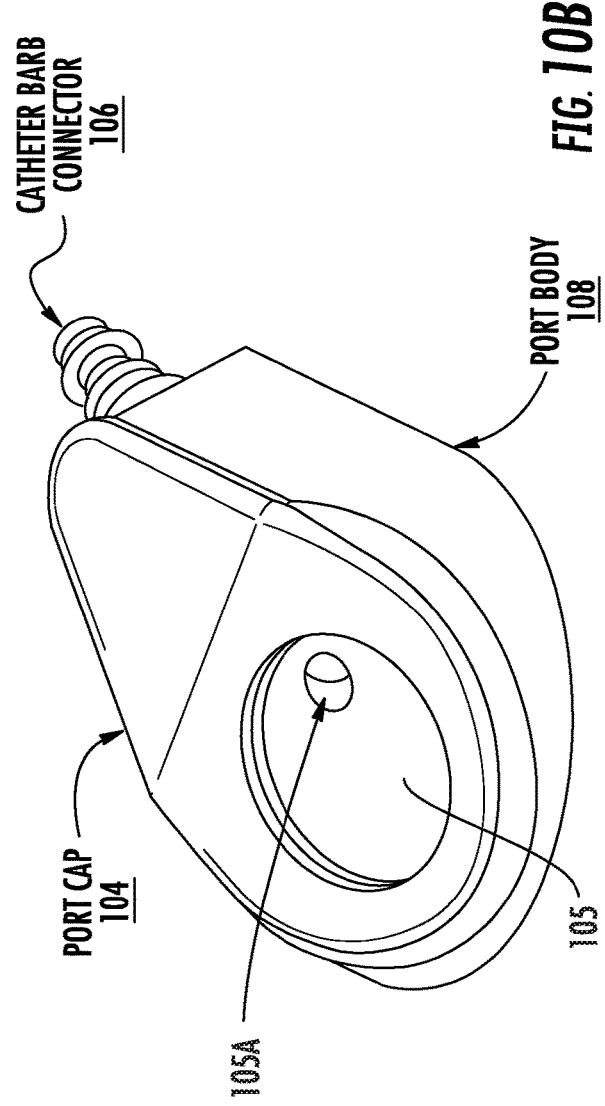
FIG. 10B is a side perspective top view depiction of the device of FIG. 10A.

Alternatively, the implant device can have an angled funnel shape or a smooth polygonal structure (such as a trapezoidal prism shape) or any other regular or irregular three-dimensional structure such as a "piano foot pedal"-shape or "computer mouse"-shape as shown in FIGS. 10A-10B.

FIGS. 10A-10B shows an implant device 100 including implant port device body 108, cap 104, port membrane 103 (not shown in FIG. 10B) (sealing opening shown with dashed lines 102) and reservoir 105 fluidly connected to catheter barb connector 106. Space 107 is an empty space for housing electronics, sensors, batteries, and communication devices. Port Membrane 103 is not shown in FIG. 10B allowing the view of channel 105A which is fluidly connected to reservoir 105.

FIG. 10A shows a device having a height 109 (for example, 0.335 inches) and a largest width dimension 101 (for example, 1.21 inches) providing a low profile, according to one embodiment of the invention.

According to preferred embodiments, the implantable device includes one or more fluid cavities for infusing medicine, therapeutics, chemotherapy drugs, supplements and/or other health related fluids or suspensions. Preferably, the reservoir in a port does not act as a storage space for medications or fluids, but rather as a place for receipt of the needle and a conduit for the medications. Alternatively, the reservoir may store medications or fluids for timed-release or administration at a later time or for time, either by direct or remote activation of the device.

Another embodiment relates to a medical implantable device for intravascular medication administration and patient monitoring, said device comprising: a) a non-collapsible housing of diameter or width to thickness ratio of 3 or greater and b) a first cavity enclosed by said housing.

Preferably, the ratio is greater than 3.5, more preferably greater than 4.0, and even more preferably greater than 4.5.

Alternatively, the ratio is less than 3 and greater than 2.

According to preferred embodiments, the housing consists in part of a permeable membrane. Preferably, the membrane enables elution of housing contents into the environment surrounding the device.

According to one embodiment the housing encapsulates a first cavity which communicates with said permeable membrane. Preferably, the cavity is adapted and/or configured to contain fluid, gaseous, powdered, granulated, or solid medication.

Another embodiment relates to a medical implantable device for intravascular medication administration and patient monitoring, said device comprising: a) a non-collapsible housing of diameter or width to thickness ratio of 3 or greater; b) a first cavity enclosed by said housing; and c) a first connector for vascular access.

Another embodiment relates to a medical implantable device for patient monitoring, said device comprising: a) a non-collapsible housing of diameter or width to thickness ratio of 3 or greater; b) a first cavity enclosed by said housing; and c) a first connector for vascular access.

Preferably, the ratio is greater than 3.5, more preferably greater than 4.0, and even more preferably greater than 4.5.

Alternatively, the ratio is less than 3 and greater than 2.

Preferably, the connector is for a catheter.

Preferably, the connector is for an optical fiber, fiber pair, or fiber bundle.

Preferably, the connector is for a wire, wire pair, or wire bundle.

Preferably, the connector is for a micro-fluidic transport via tubule, wicking paper, or wicking fiber.

Preferably, the connector is for an RNA micro-array chip.

According to preferred embodiments, the implantable device comprises, within at least one reservoir or cavity, medicine, therapeutics, chemotherapy drugs, supplements and other health related fluids or suspensions.

Preferably, the implantable port device includes a first fluid cavity having a volume ranging from 0.1 to 50 ml, preferably 1 to 10 ml, and more preferably 1 to 5 ml.

Preferably, the first fluid cavity has a volume shaped like a disc or oval.

Preferably, the implantable port device further comprises a second fluid cavity (e.g., dual-reservoir or dual-lumen port).

According to preferred embodiments, the implantable port device includes a cap covering a top opening allowing access to the fluid cavity (e.g., first fluid cavity) within the device. Preferably, the cap forms the top of the housing and is made of self-sealing, biocompatible material. Preferably, the cap comprises silicone, more preferably consist essentially of silicone.

Another aspect of the invention relates to implantable port devices having one or more electronic device(s) and/or sensors incorporated therein. Preferably, the electronic device(s) and/or sensors are configured and/or adapted to facilitate localization of the implanted device and/or transmit information to and from the implanted device and/or monitor the implanted device and/or patient. According to particularly preferred embodiments, the one or more electronic device(s) and/or sensors are adapted to analyze data and/or measurements (e.g., identify irregular measurements).

One embodiment relates to a medical implantable port device used for intravenous medication administration, the device comprising:
 a) a housing made of a rigid biocompatible material;
 b) a first fluid cavity within the housing;
 c) a cap forming the top of the housing and made of self-sealing, biocompatible material;
 d) at least one electronic identifier within the reservoir or in contact with the first fluid cavity or on an outer surface of port reservoir forming the first fluid cavity or within the device housing but not in contact with the first fluid cavity; and
 e) at least one data storage device or tag.

The term "fluid" as used herein refers to liquids including a liquid containing a solid dissolved in a liquid solute.

Another embodiment relates to a medical implantable port device used for intravenous medication administration, the device comprising:
 a) a housing made of a biocompatible material;
 b) a first fluid cavity within the housing;
 c) one or more electronic components configured to (i) transmit data from the device to an external computer system, (ii) transmit localization data to the external computer system; or (iii) both (i) and (ii).

Preferably, the external computer system is a handheld device. For example, the hand-held devices shown in FIGS. 6, 7, 8, 13, and 14.

Preferably, the one or more electronic components comprise at least one electronic identifier either (i) within the reservoir or in contact with the reservoir or (ii) on outer surface of port reservoir or (iii) within the device housing, but not in contact with first fluid cavity or reservoir. Preferably, at least one electronic identifier comprises one or more radio-frequency identification (RFID) tag(s), more preferably an array of radio-frequency identification (RFID) tag(s).

Preferably, at least one electronic identifier comprises a centrally located radio-frequency identification (RFID) tag.

According to preferred embodiments, the implantable port device further comprises a transmitter to transmit data to another device or information network via wireless, cellular, or Bluetooth or other electronic or telemetric transmission.

Specifically, wireless communication means may include cellular, mobile phone, am/fm radio, WiFi, bluetooth, other near-field communication; RFID by RF signal and antenna resonant response, other radio signal, magnetism, or magnetic field. Cellular or mobile signaling or communication includes any of the following signal protocols or technologies: time-division multiple access (TDMA), frequency-division multiple access (FDMA), code-division multiple access (CDMA), orthogonal frequency-division multiple access (OFDMA), polarization-division multiple access (PDMA), Global System for Mobile Communications (GSM), General Packet Radio Service (GPRS), cdmaOne, CDMA2000, Evolution-Data Optimized (EV-DO), Enhanced Data Rates for GSM Evolution (EDGE), Long Term Evolution (LTE), Universal Mobile Telecommunications System (UMTS), Digital Enhanced Cordless Telecommunications (DECT), Digital AMPS (IS-136/TDMA), Integrated Digital Enhanced Network (iDEN), or WiMAX (IEEE 802.16). WiFi communication includes IEEE 802.11 specification of media access control (MAC) and physical layer (PHY) specifications for implementing wireless local area network (WLAN) computer communication in the 2.4, 3.6, 5, and 60 GHz frequency bands. Bluetooth communication includes any of the following protocols: Asynchronous Connection-Less [logical transport] (ACL), Synchronous connection-oriented (SCO) link, Link management protocol (LMP), Host Controller Interface (HCI), Low Energy Link Layer (LE LL), Logical link control and adaptation protocol (L2CAP), Bluetooth network encapsulation protocol (BNEP), Radio frequency communication (RFCOMM), Service discovery protocol (SDP), Telephony control protocol (TCS), Audio/video control transport protocol (AVCTP), Audio/video data transport protocol (AVDTP), Object exchange (OBEX), Low Energy Attribute Protocol (ATT), Low Energy Security Manager Protocol (SMP). Near field communication is typically 13.56 MHz and including any frequency in the 13-14 MHz range.

Preferably, the implantable device is adapted to transmit data to and from smartphones and/or computers and/or a cellular network (e.g., adapted by the selection, design and configuration of the device components). For example, the implantable device is adapted to transmit data to and from an app (software application) on a smartphone or other commercially available handheld mobile device (e.g., a tablet) or other computer device (e.g., electronic watch or laptop).

According to preferred embodiments, the device is equipped with an audio, visual, or vibrational alert to signal device wearer, caregiver of wearer, or emergency responder personnel. Preferably, the alert is related to said fluid cavity by function or status. Preferably, alert is related to blood sampling result or status, vital sign monitoring result or status, motion sensing result or status such as a fall or seizure activity.

Preferably, the implantable port device is powered by the same bandwidth used in smartphones and/or computer.

Current implantable ports have no means of providing the following features or functionality:
 a) Remote identification of the port or patient.
 b) Remote or electronic localization.
 c) Remote communication.
 d) Monitoring of physiologic parameters like temperature, heart rate, blood pressure, rhythm, patient motion, activity, sleep, etc.
 e) Monitoring of blood lab values such as complete blood count (CBC), chemistry, glucose, etc.

According to particularly preferred embodiments of the invention, the implantable port device is configured and adapted to provide the following advantages:
 a) Low profile as to be nearly unnoticeable to the patient and others (friends, family, co-workers, etc.).
 b) High precision remote localization for access using RFID or similar technology.
 c) Identification of port and patient through RFID that allows communication with EMR and centralized database or managing the port and tracking cancer therapy.
 d) Localization through remote powering and activating of LEDs.
 e) Monitoring and transmission of physiologic data including, but not limited to, temperature, heart rate, rhythm, central venous pressure, etc.
 f) Testing and transmitting laboratory parameters such as CBC values, chemistry panels, blood glucose, etc.
 g) MRI safe.

h) Tolerant of large radiation exposures.
i) Low levels of CT artifact (beam-hardening/attenuation of radiation)
j) Anti-thrombogenic coating/eluting.
k) Antimicrobial coating/eluting.

Preferably located within, or attached to, the reservoir but not in fluid communication with the blood is an electronic means of or electronic device adapted for localization, identification, and data transfer. Although one preferred design uses radio frequency identification (RFID) technology, it is within the scope of the invention to utilize other technologies such as near field communication or telemetry. This localizing technology could be comprised of a single centrally located tag (e.g., tag 24 shown in FIG. 2B) or an array of multiple tags (e.g., array 58 shown in FIG. 5).

After implant and during use, the reservoir is accessed through the skin preferably using a non-coring needle. Referring to FIG. 3A, needle point 39 of bent Huber-type needle 38 is shown above the center and close to being inserted into the cap of implant 30. This could be performed with needles currently used and available on the market. One preferred method of access would utilize a flexible catheter (e.g., catheter 35 shown in FIG. 3B) disposed over a solid, non-coring, stylette style needle (e.g., solid, non-coring, stylette style needle 37 also shown in FIG. 3B).

Figure 3B:
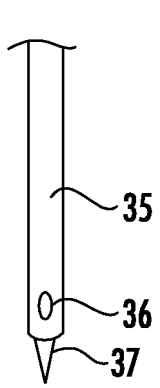
FIG. 3B is a side view depiction of a needle-catheter access system according to one embodiment of the invention.
Figure 4A:
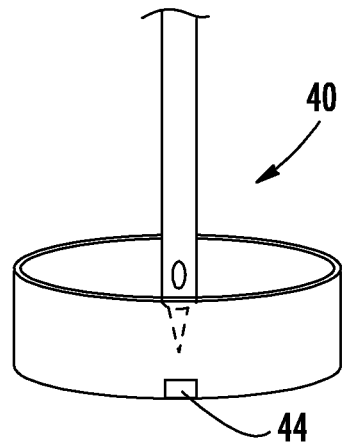
FIG. 4A is a side perspective view of the port reservoir accessed with a flexible catheter of FIG. 3B.
Figure 4B:
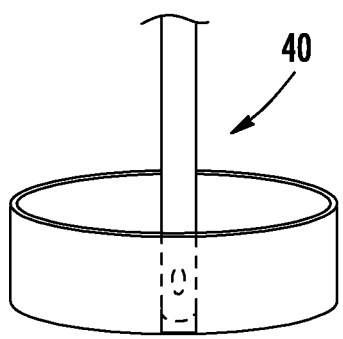
FIG. 4B is a side perspective view of the implant having a port reservoir with the flexible catheter of FIG. 3B fully inserted into the implant reservoir.
Figure 4C:
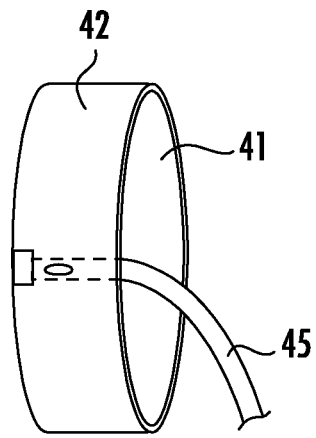
FIG. 4C is a side view of the implant device of FIG. 4B with the fully inserted catheter.

FIG. 4A shows the needle 37 of FIG. 3B inserted into the reservoir of implant device 40 with electronic device 44 (e.g., RFID chip) adapted to facilitate guiding the needle 37 into the port device. Once access is obtained, the needle 37 is removed leaving the catheter 45 in place for medication administration or blood aspiration as shown in FIG. 4B and FIG. 4C. The catheter and/or access needle may have one or multiple side holes (e.g., hole 36 shown in FIG. 3B) to facilitate medication administration or blood aspiration, or perform infusion through an end-hole only. As the port reservoir is preferably designed to have a low-profile and therefore be nearly unnoticeable in the patient and difficult for the caregiver to locate, it will require a system, device or means of localization for access. This is preferably accomplished with a handheld detection device (e.g., device 60 shown in FIG. 6). The handheld device is preferably adapted for localizing the implanted device and, preferably also identifying the implanted device and, more preferably, also the patient. Preferably, the detection device includes a targeting feature that will guide the user to the location of the port. This targeting feature could include audio commands or localization lights (e.g., lights 61 in FIG. 6), and could also employ lasers for guidance (e.g., crossing laser lights forming a cross mark 63 in FIG. 6 or a wand that provides localization signals).

For simplicity, preferred embodiments of the present invention relates to a single-reservoir, single-lumen device, but the novel concepts contained herein are not limited to any one configuration of implantable medical device including devices with two or more reservoirs for different medications or therapies and/or multiple light emitting devices (as described below).

Figure 9:
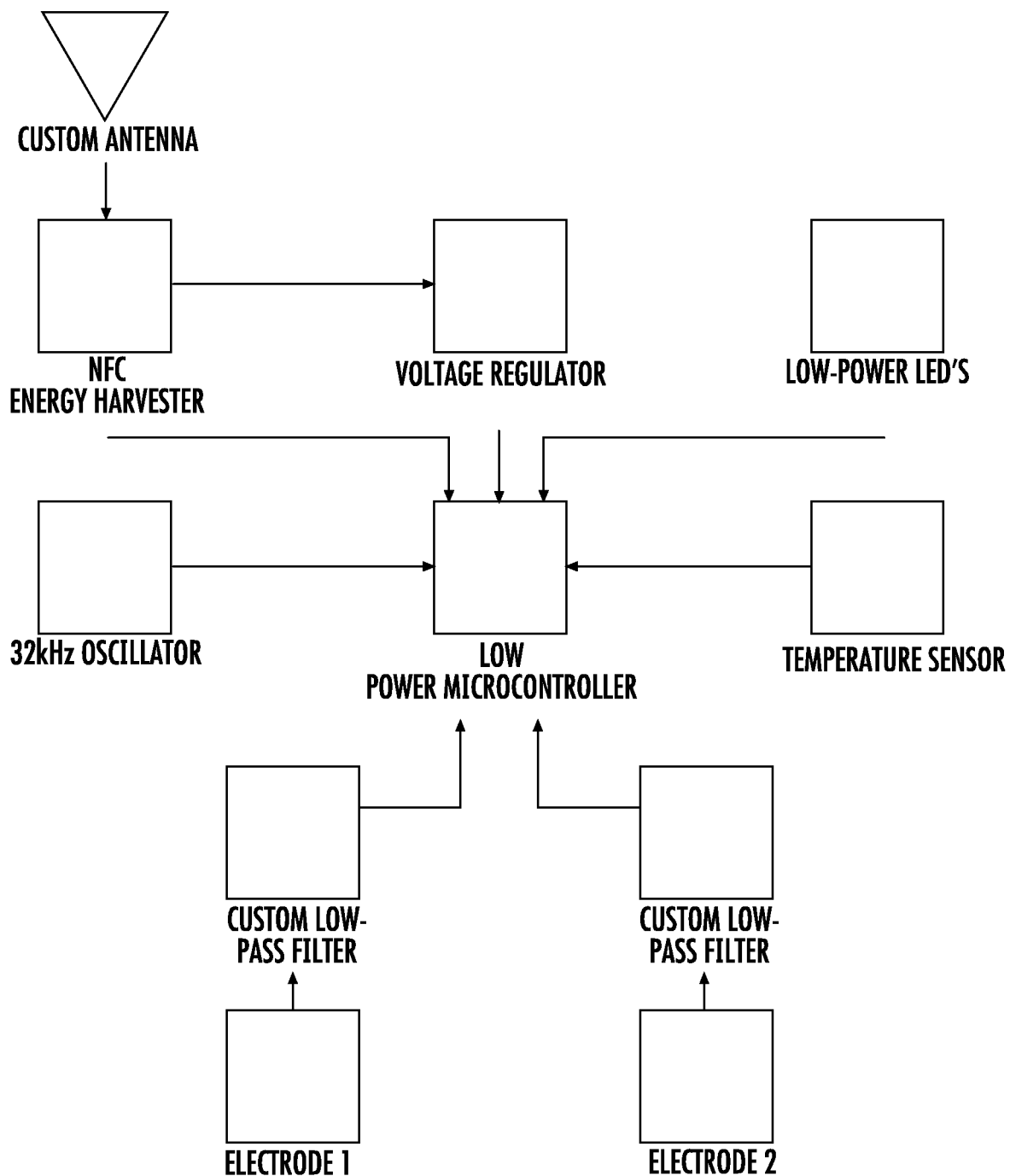
FIG. 9 is an exemplary schematic diagram of an implant device block diagram according to another embodiment of the invention.

FIG. 9 is a schematic diagram of an implant device according to one preferred embodiment showing one configuration of the components of the implant device including Custom Antenna (e.g. for transmitting data to and from the implant device to external computer devices), NFC Energy Harvester, Voltage Regulator and Low-Power LEDs, each preferably electronically connected to a Low Power Microcontroller. FIG. 9 also shows a Temperature Sensor (to measure the temperature of the patient), Oscillator and two Custom Low-Pass Filters (connected to Electrodes).

Another aspect of the invention relates to implantable ports having one or more lights or light emitting diodes (e.g., LEDs) or other light emitting devices to facilitate locating the port and/or the orientation of the port under a patient's skin. According to preferred embodiments, the implanted device has a low profile making locating the device using direct palpation difficult and/or uncomfortable to the patient. Accordingly, the invention employs light emitting diodes producing light sufficient to be seen through the patient's skin and thus allowing the implanted device and, preferably, the device's orientation to be determined.

One embodiment of the invention relates to a medical implantable port device used for intravenous medication administration, the device comprising:
a) a housing made of a rigid biocompatible material;
b) a first fluid cavity within the housing;
c) a cap forming the top of the housing and made of self-sealing, biocompatible material; and
d) an array of two or more lights capable of remote activation.

Preferably, the array of two or more lights emit sufficient light to be visible through the layer of the patient's skin over the implanted device. According to preferred embodiments, the level of light emitted can be adjusted using an external device (e.g., handheld devices described herein) from a low level to a higher level until the light can be visible to the caregiver.

Preferably, the array of lights includes three or more lights, more preferably four or more lights, even more preferably six or more lights. Preferably the light could also be a continuous circular light, oval, or other geometric or ornamental design.

Preferably, the lights are located on the top surface of the implanted device facing away of the inner body of the patient and preferably are located adjacent and facing the overlying patient skin covering the implanted device, for example, LEDs 131 in FIG. 11B, and LEDs 151 in FIG. 12B.

Another aspect of the invention relates to handheld or portable devices configured to locate implantable ports and/or transmit and/or receive data from the implantable port.

One embodiment of the invention relates to a handheld identification device, for use with a medical implant having a port, for locating the port after implantation of the medical implant in a patient, the device comprising:
(a) a transmitter adapted to generate an interrogation signal, wherein an electronic tag within the implant operates in response to the transmitted interrogation signal to generate a tag response signal;
(b) an antenna or antenna system operable by the transmitter for transmitting the interrogation signal and receiving the tag response signal;
(c) a power source or means of remote power generation to power the electronics on the port device in the absence of a battery and;
(d) a localization system for processing the tag response signal to locate the port of the medical implant.

According to one preferred embodiment, the power source or means of remote power generation is a battery, electrical generator, a power outlet or other power source.

Figure 6:
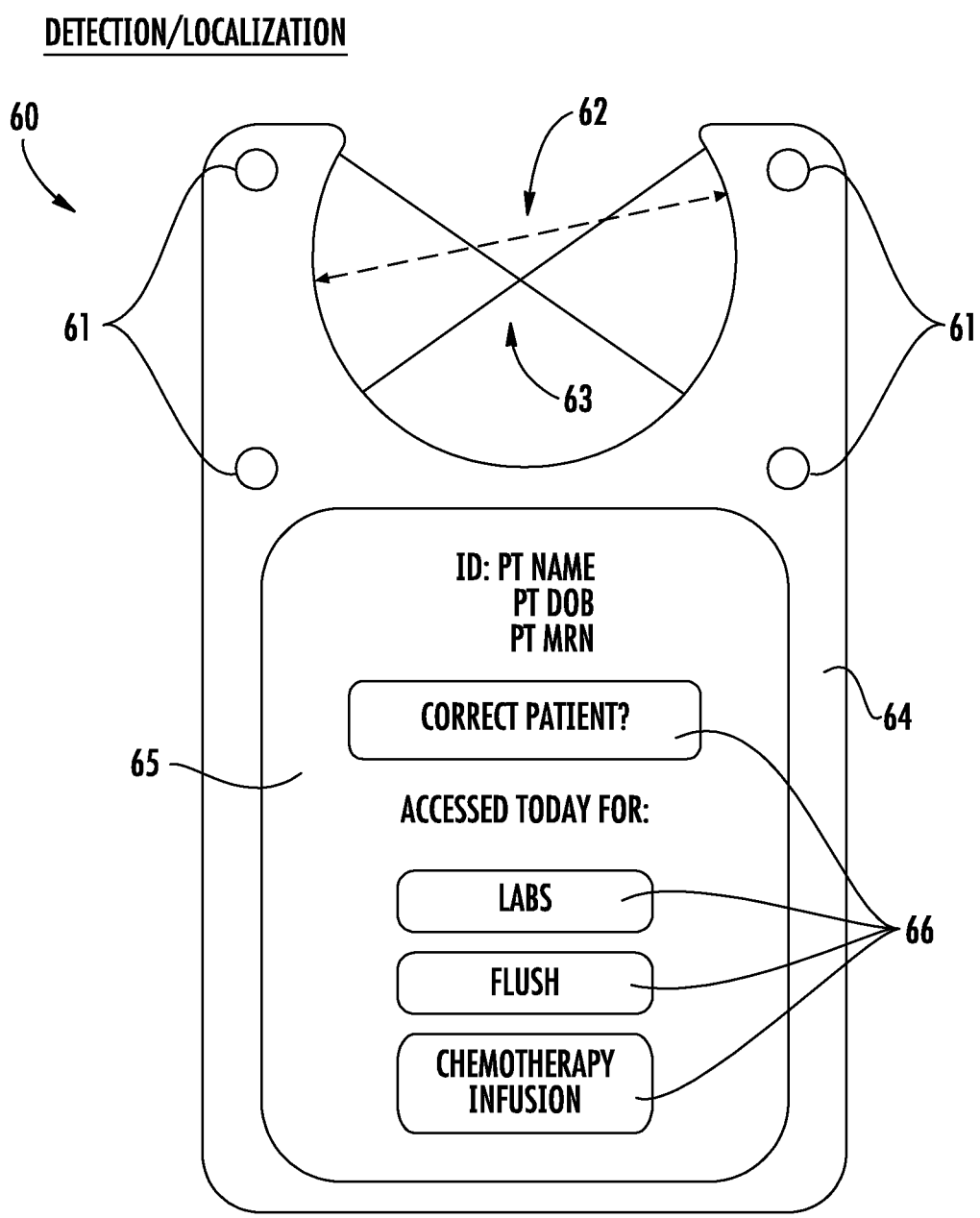
FIG. 6 is a top view of the handheld detection and data entry device according to one embodiment of the invention.

FIG. 6 illustrates a handheld device 60 according to one embodiment of the invention including housing 64 incorporating electronic display 65. Preferably display 65 is an interactive display allowing the user to input information and/or select options by touching icons 66 shown on the display. According to preferred embodiments, the display 65 requests the user to confirm the patient identification, the patient's medical information, the location of the implanted device, the status of the implanted device, the therapeutics, drugs, or medicines being provided to the patient from the implanted device, and other related information. Preferably, the handheld device 60 comprises an optical scanner to read bar codes, labels, or the like.

According to preferred embodiments, the handheld device is adapted and/or configured to determine the location and, preferably, the orientation of the implanted device. Preferably, the handheld device includes an opening or window (as shown in FIG. 6 having an approximate diameter shown as dashed line 62). The opening or window is preferably circular. Alternatively, the window is rectangular or other shape.

Figure 13B:
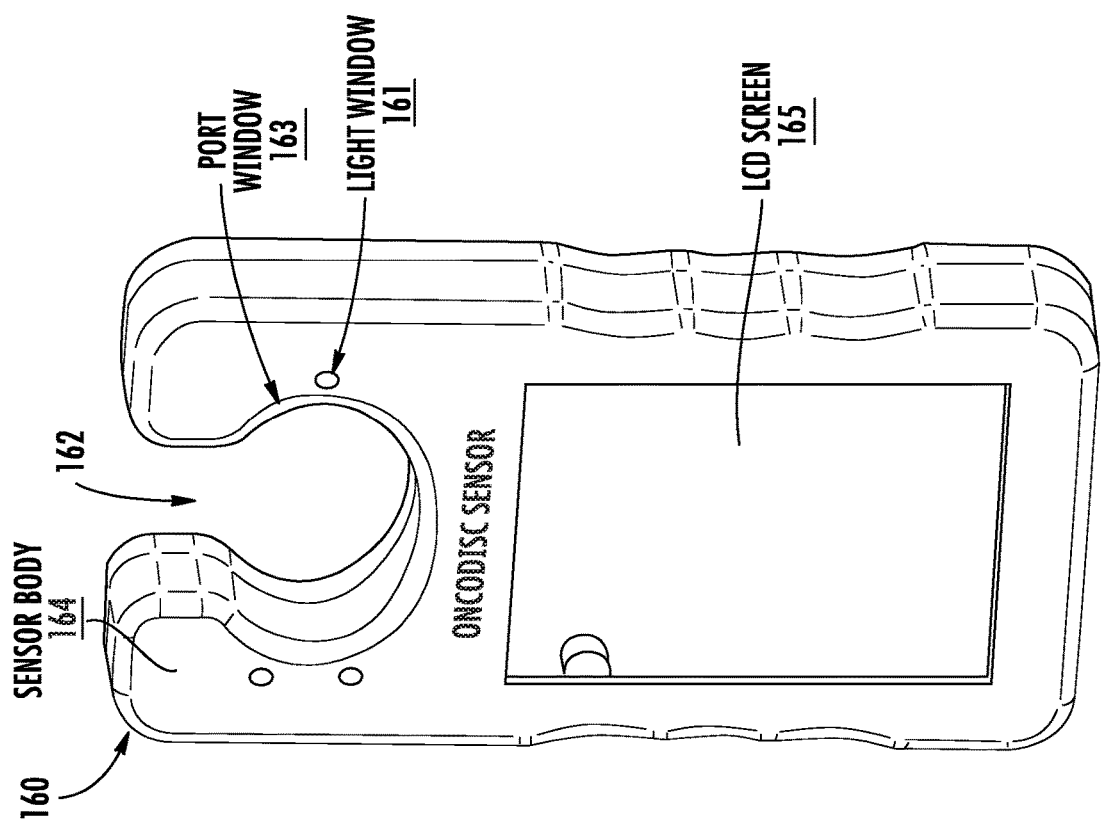
FIG. 13B is an angled front view of the device of FIG. 13A.
Figure 13A:
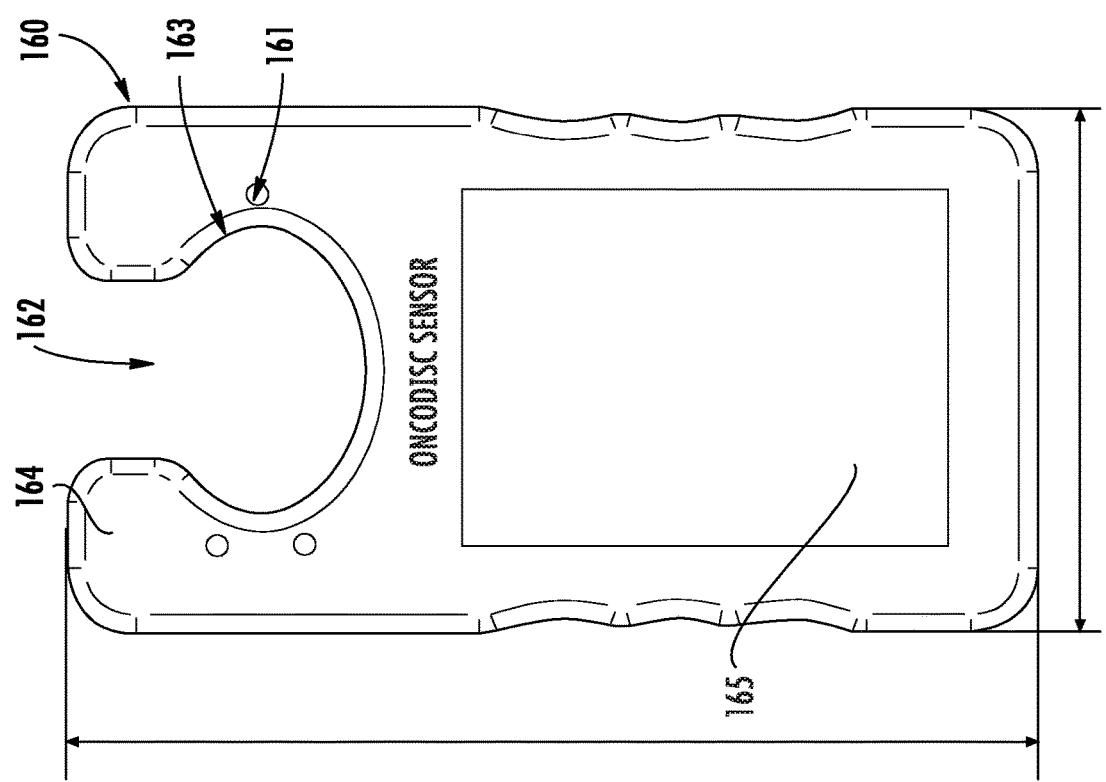
FIG. 13A is a front view of a hand-held sensor device according to one embodiment of the invention.

FIGS. 13A and 13B is a drawing of a handheld device 160 according to another embodiment including sensor body 164 with the port window 163 including an open top 162. Device 160 comprises LCD screen 165 and light windows 161.

Figure 14B:
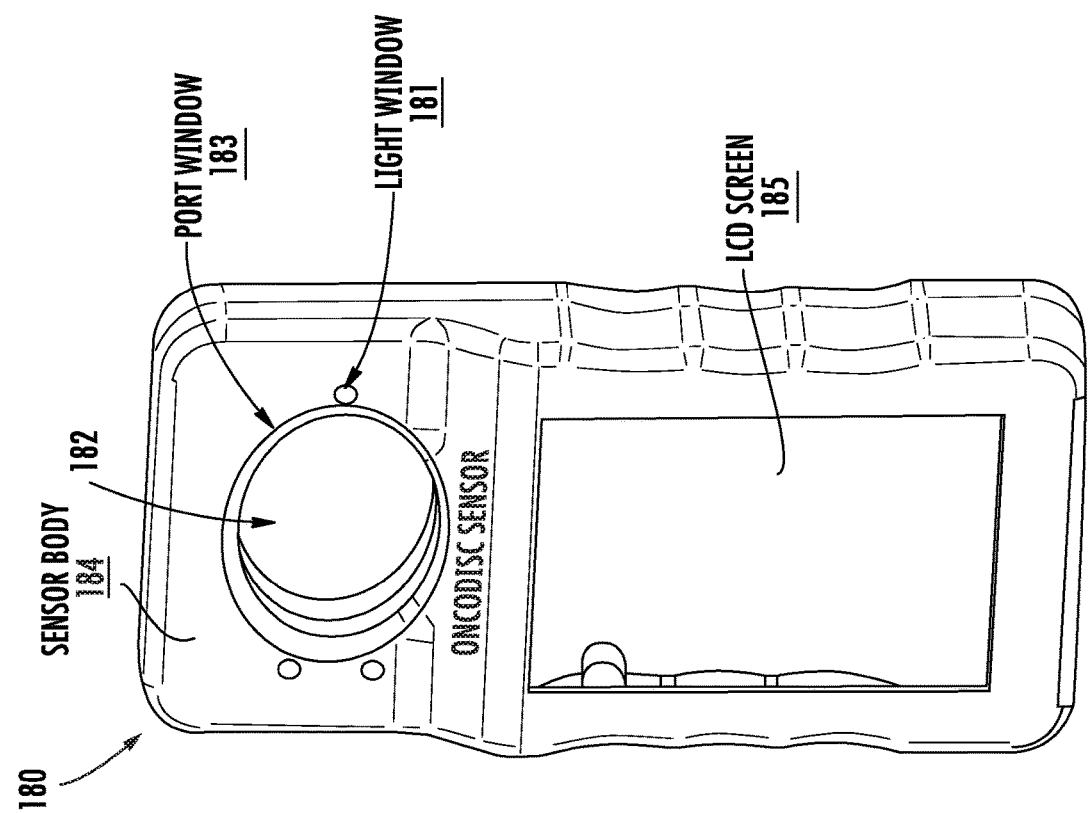
FIG. 14B is an angled front view of the device of FIG. 14A.
Figure 14A:
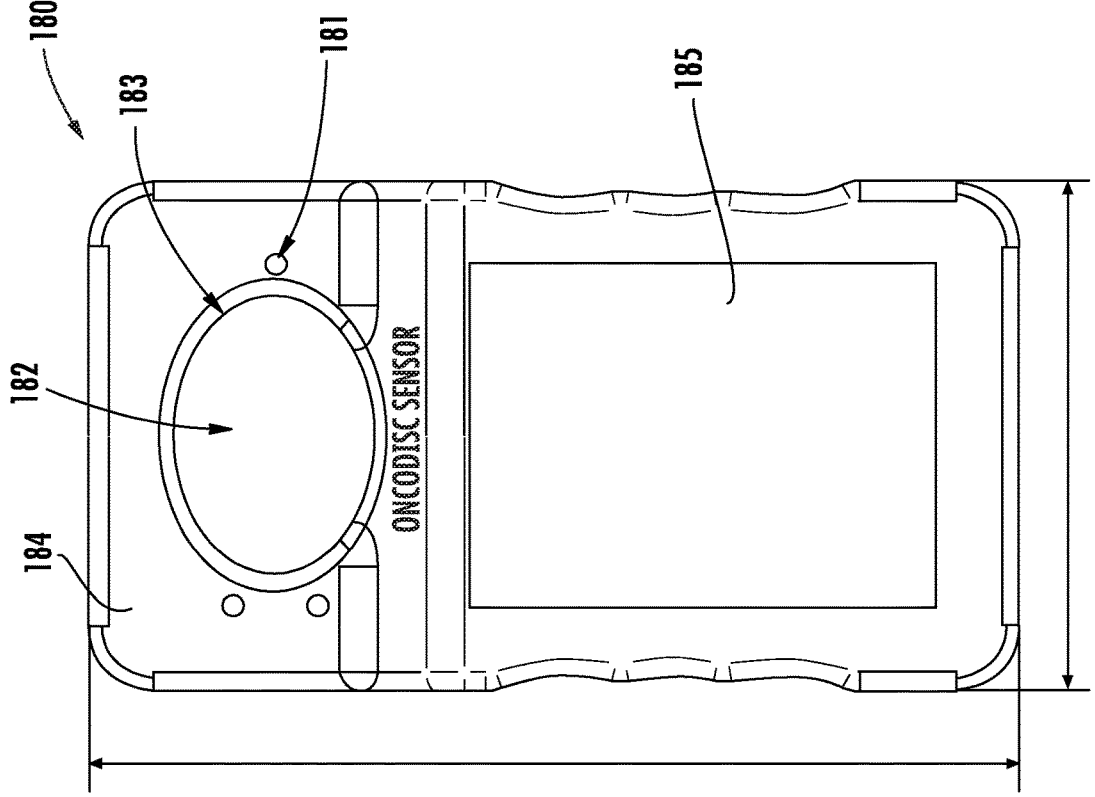
FIG. 14A is a front view of a hand-held sensor device according to one embodiment of the invention.

FIGS. 14A and 14B is a drawing of a handheld device 180 according to another embodiment including sensor body 184 with the port window 183 without an open top. Device 180 comprises LCD screen 185 and light windows 181. Center 182 of port window 183 is also shown and indicates the proximate location for the needle insertion.

Preferably, the handheld device is adapted to provide power for the electronics on the implanted port, for example, when the port does not have an internal power source or battery or when the port does not have enough power. According to preferred embodiments, the power source of the implant device can be wirelessly charged, preferably by the handheld device.

According to preferred embodiments, the handheld device is capable of activating one or more emitting devices on the implanted devices to facilitate locating the implanted devices.

Preferably, the transmitter is a radio frequency transmitter.

According to preferred embodiments, the device further comprises a touch screen (e.g., display 65 in FIG. 6 or 165 in FIGS. 13A and 13B) interface capable of displaying information about the port and the patient. Preferably, the touch screen is also capable of data entry to allow the user to enter data regarding the use of the port and/or information about the patient.

Preferably, the device further comprises a targeting system capable of emitting audio commands, localization lights and/or one or more guidance lasers. For example, FIG. 6 shows cross-mark 63 preferably generated by lasers showing the optimal target for inserting a needle into the implanted port.

Preferably, the device further comprises electronics capable of determining the location of the port of the implant in three-dimensional space and extracting the information embedded within the RFID tags of the implant.

Preferably, the device further comprises at least one display, preferably, the display is a screen.

Another embodiment of the invention relates to handheld devices adapted or configured to help locate the implanted device. Preferably, the handheld device and/or implanted device includes one or more localization components or systems for facilitating implant location and, preferably, orientation.

According to preferred embodiments, the localization system includes one or more lights or light emitting diodes or other devices (e.g., on the implanted device) and/or sensors for detecting light (e.g., on the handheld device). For example, according to preferred embodiments, the handheld device uses a localization system that comprises one or more sensors within the handheld device and one or more lights in the implanted device.

Figure 7:
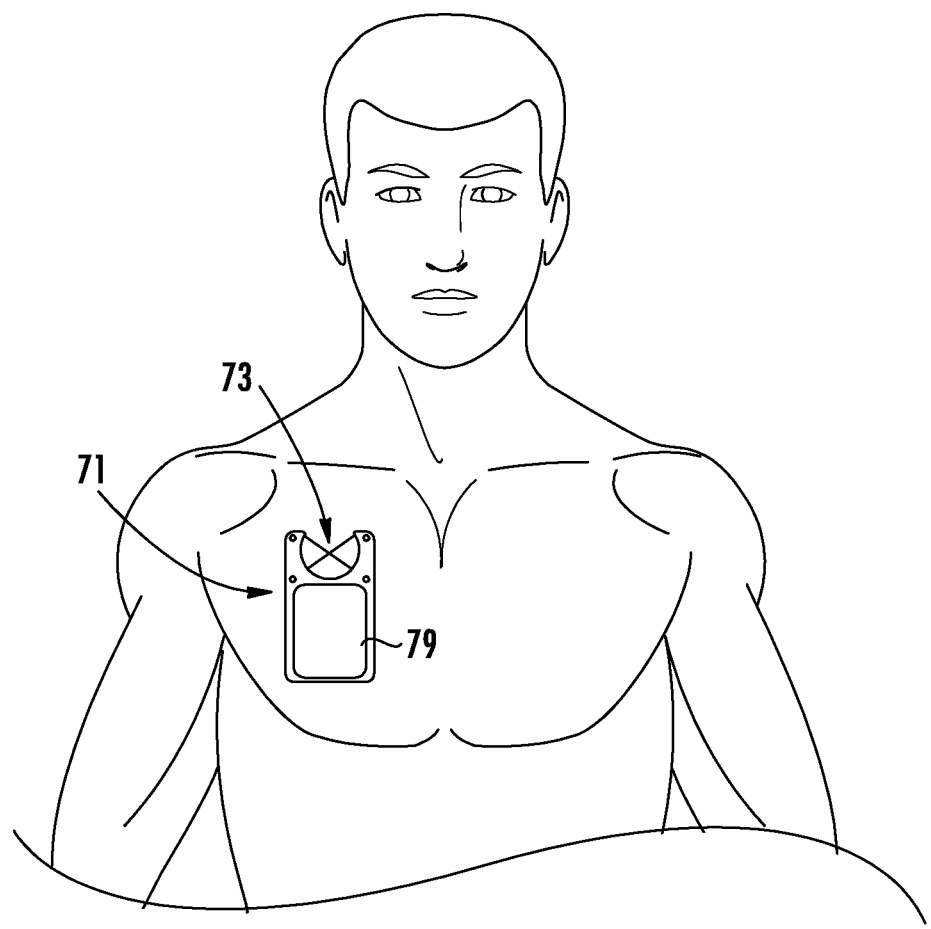
FIG. 7 is a front view of a handheld detector according to the invention in place over the chest wall of a patient when being used to localize the implanted port reservoir (not shown).

Preferably, the handheld device further comprises signal lights (for example signal lights 61 as shown in FIG. 6) that signal to the user the location and/or orientation of the implanted device relative the handheld device. For example, referring to FIG. 6, the signal lights 61 would preferably all light up when the handheld device (and cross-mark 63) are lined up correctly over the implanted device. For example, as shown in FIG. 7, handheld device 71 is held adjacent to the patient's chest where the implanted device (not shown) is implanted. The cross-marks 73 (preferably generated with laser lights) pin point the location of the port of the implanted device for needle insertion and display 79 can display information relating to the implanted device and/or patient and/or related information. In FIG. 7, four signal lights are shown and configured to confirm the location and orientation of the handheld device relative to the implanted device.

Preferably, the localization system includes an array of lights to assist in localization, for example signal lights on the handheld device and/or emitting lights (e.g., LEDs on the implanted device).

Preferably, the implanted device includes both RFID tags and LED lights within the implant adapted and/or configured to localize the port.

Preferably, the device uses LED lights within the implant to localize the port and RFID within the implant for data storage and/or data transmission.

According to preferred embodiments, the handheld device can electronically communicate with the implanted device. Preferably, the handheld device further comprises a communication system for two-way communication between the device and a centralized computer system. Preferably, the device is adapted to provide instructions to the user for precise localization for needle access of the port. Preferably, the instructions comprise audible, visual, tactile feedback or any combination thereof.

Preferably, the localization system comprises two or more openings through the handheld device configured to line up with an array of LEDs on the implant. For example, referring to FIG. 6, signal lights 61 could be replaced with openings that can be aligned over emitting lights from the implanted device to confirm proper orientation of the handheld device over the implanted device.

According to preferred embodiments, the handheld device and/or implantable device are adapted to provide data storage, remote sensing and identification features, systems design and physiologic monitoring (e.g., temperature, heart rate, blood pressures, activity levels, etc.).

Preferably, the electronics of the handheld device are capable of data-retrieval from the implant and communication with a centralized computer system or other computer system.

Preferably, the centralized computer system includes local electronic medical records and a database that monitors the use of each implant.

Preferably, the device is adapted to receive data from one or more sensors monitoring the patient, preferably body temperature, heart rate, blood pressure, and/or activity. The handheld localization device will also preferably be used as a tool for data transmission. It will have a touch screen interface (e.g., display 65 in FIG. 6) that will both display information about the port and the patient, as well as allow the user to enter data regarding the use of the port as well as information about the patient. Any data retrieved from the device is preferably transmitted to the electronic medical record for local storage and interpretation, but also to a centralized database. This centralized database can be used to alert patients and their healthcare providers regarding information such as when maintenance is required or there is a malfunction or when the patient's physiologic parameters indicate clinical deterioration and a need for medical evaluation. According to preferred embodiments, the devices monitor vital signs or other physiologic parameters and transmit that data to both the medical record and the centralized database.

Preferably, the localization device can also have data input feature that allows for communication with EMR and centralized database.

Preferably, the handheld device is configured to allow a user to input:
  Verify patient/device based on RFID
  Port flush
  Labs drawn
  Chemotherapy infused
  Vital signs
  Preferably, the user interface includes:
    Target localization: User can be alerted that the localizer is in position when directly over the port using one or more of the following:
      1. Lights
      2. Sound
      3. Laser target
      4. Physical target (sterile covering with center hole for needle)

Preferably, the input interface comprises an easy to use touch screen that communicates with EMR and centralized database.

Figure 15:
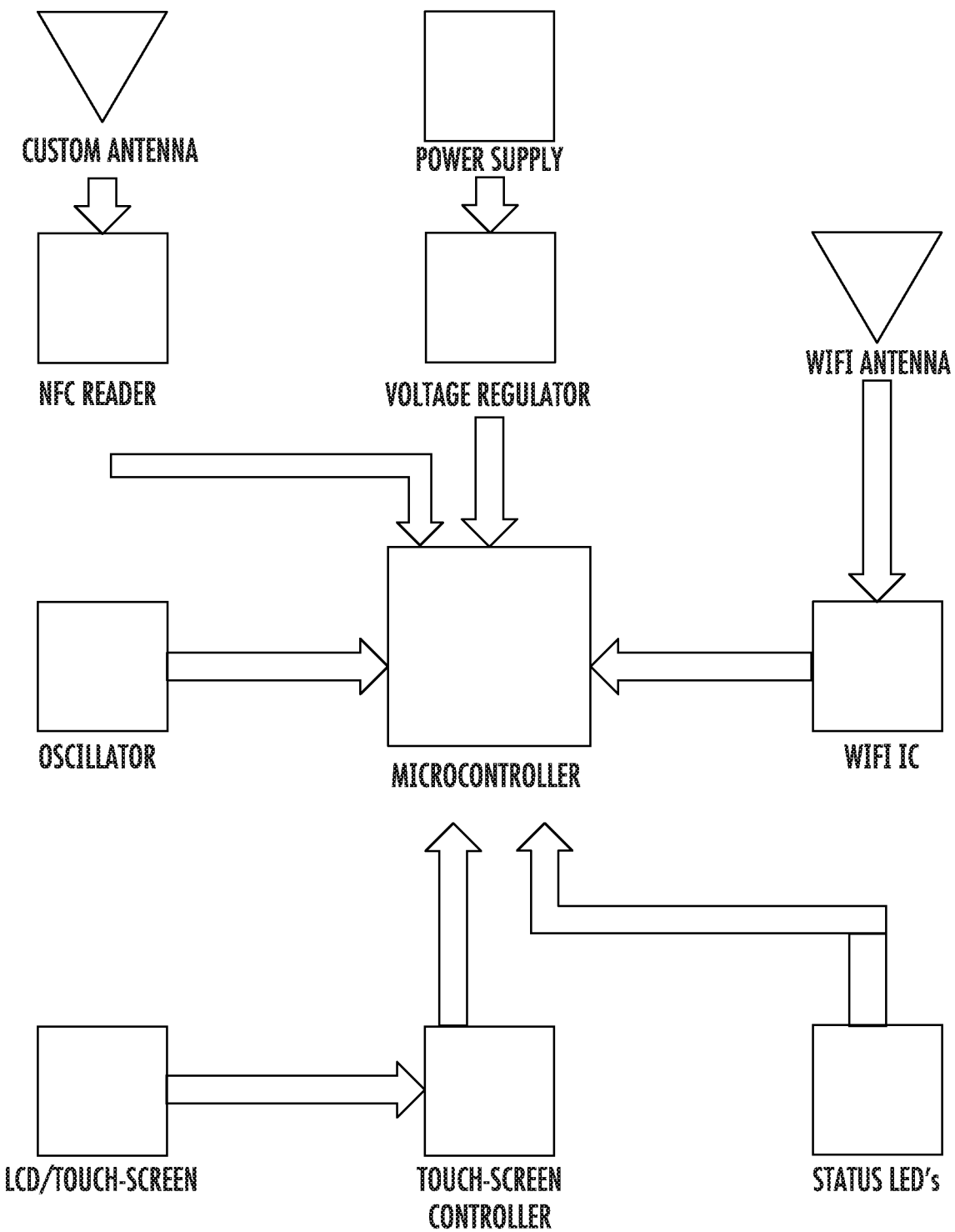
FIG. 15 is an exemplary block diagram of a hand-held reader device according to another embodiment of the invention.

FIG. 15 is a schematic diagram of the components of a handheld device according to preferred embodiments of the invention.

Another aspect of the invention relates to a system including one or more computers for managing and monitoring one or more implantable devices preferably using one or more of the handheld devices described herein.

One embodiment relates to a system for the management and monitoring of implantable ports used for intravenous medication administration comprising:
  (a) a computer system comprising electronic medical records and a database that monitors use of each implantable port;
  (b) an implantable port capable of intravenous administration of one or more medications or medical agents when implanted into a patient; and
  (c) a handheld identification device adapted to locate the implantable port after implantation in a patient.

Preferably, the system includes two or more, preferably five or more implantable ports for implanting into different patients.

Preferably, the handheld identification device comprises a communication system for transmitting and receiving data from the implantable port and/or the computer system. The handheld device used for communication is capable of being a custom designed device also configured for localization and port access as described above or could preferably be a commercially available smart phone, tablet computer, laptop computer, desktop computer, wearable device such as a smart watch, or any other commercially available computer capable of remote communications.

Figure 8:
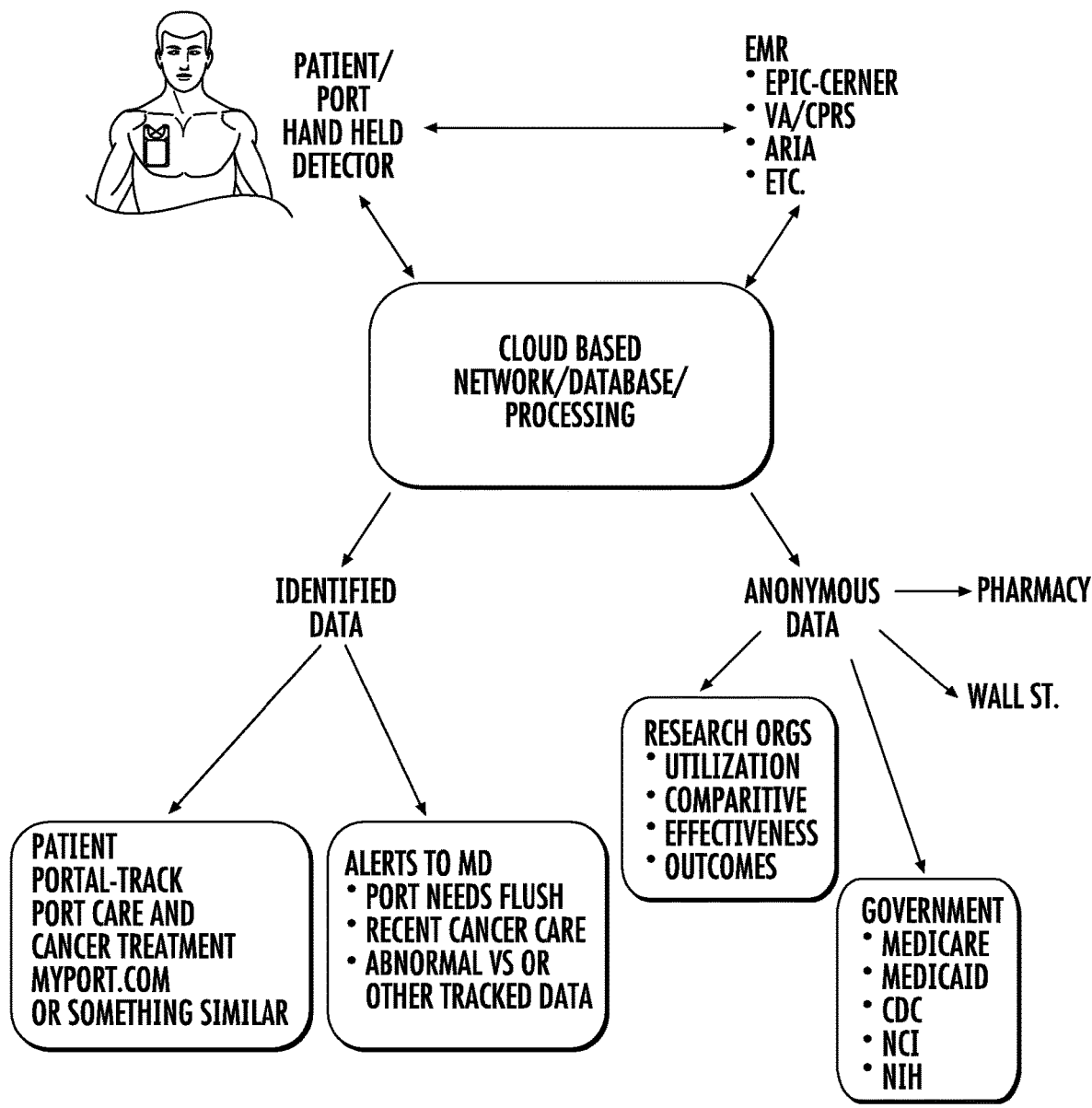
FIG. 8 is an exemplary schematic diagram of the data network according to one embodiment of the invention.

FIG. 8 is a block diagram of a system according to one embodiment of the invention and a patient shown with a handheld device according to one embodiment of the invention. The system shown in FIG. 8 includes a Cloud Based Network/Database/Processing subsystem configured to electronically communicate with the handheld device shown adjacent the patient (and preferably also communicates with the implanted device via the handheld device). Preferably, the Cloud Based Network/Database/Processing subsystem includes or is electronically connected to (via wire or wireless) an identified Data database(s) and, preferably, also electronically connected to (via wire or wireless) an Anonymized Data or otherwise privacy compliant database(s). Preferably, the Identified Data database(s) contains data relating to the patient, the patients treatment and history, information relating to illness, disease or abnormal symptoms including recent updates on treatments, drugs, side effects, therapies, care and other medical information (for example, portal-tracking of the implant device, port care and cancer treatment being provided by the implant, trackmyport.com (e.g., an online website for managing the implant device and care) or the like). Preferably, the Anonymized Data database(s) is configured to electronically communicate with Research Organizations (e.g., to provide and exchange information relating to the implant utilization, comparative results and information, effectiveness, side-effects or technical issues, outcomes and the like), Government entities (e.g., Medicare, Medicaid, CDC, NCI, N and the like to exchange permission requests and approvals, authorizations, data, information and the like). Preferably, the Anonymized Data database(s) and/or Identified Data database(s) are configured to electronically communicate with pharmacies, pharmaceutical/biotech companies, financial entities and the like.

Advantageously, the system's ability to collect and aggregate anonymous or anonymized data from many different implanted devices and patients located in different regions will allow regulators, researchers, and medical professionals to track and analyze the aggregated data to better predict outcomes, improve the treatments, identify issues or problems, etc. In addition, the ability to transmit data directly to government agencies (e.g., FDA) and biotech/pharma companies allows for improved clinical trials as data can be obtained from many implanted devices more quickly, more accurately and with less expense. Advantageously, the system could provide tracking of compliance for clinical trials. Moreover, the ability to collect aggregated data (e.g., "Big Data") provides opportunities to identify trends, events, and related information. Machine learning, artificial/augmented intelligence, and other data analytics tools can be utilized to predict adverse outcomes in individual patients as well as identify trends in therapy and outcomes in order to improve overall medical care and alert the device wearer, caregivers, and emergency response teams. Yet another aspect of the invention relates to methods of using the devices and systems described here.

One embodiment of the invention relates to a method for introducing a needle into an implanted port, the method comprising:
  (a) locating the port of the implanted port using localization signals emitted by the implanted port using a handheld detector; and
  (b) accessing the implanted port with the needle using electronic localization instructions provided by the handheld detector.

Preferably, the method further comprises electronically receiving data from the implanted port using the handheld detector.

Preferably, the locating includes the handheld detector providing visual, audio, or tactile feedback for localizing the port.

Preferably, the locating uses visual tools (e.g., lights emitted from the implanted device) for localizing the port.

Preferably, the localization signals are light, preferably emitted from LED lights within, or connected to, the implanted port.

Preferably, the localization signals are emitted by one or more emitting devices within, or connected to, the implanted port.

Preferably, the localization signals are RFID signals emitted by one or more RFID emitters within, or connected to, the implanted port.

The various features of the above description, representative examples, and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

The scope of the present devices, systems and methods, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

While exemplary embodiments have been shown and described above for the purpose of disclosure, modifications to the disclosed embodiments may occur to those skilled in the art. The disclosure, therefore, is not limited to the above precise embodiments and that changes may be made without departing from its spirit and scope. Various modifications, uses, substitutions, combinations, improvements, methods of productions without departing from the scope or spirit of the present invention would be evident to a person skilled in the art.

What is claimed is:

1. An implantable, single-reservoir port device comprising:
    a housing made of a biocompatible material and having a width-to-height ratio of greater than 3.0;
    a single fluid reservoir within the housing;
    a self-sealing cap covering the fluid reservoir;
    a ridge formed in an upper surface of the housing and circumferentially surrounding at least a portion of the fluid reservoir;
    a catheter connector in fluid communication with the fluid reservoir, the catheter connector configured to be mated to a catheter;
    a battery disposed within the housing, wherein the battery is wirelessly rechargeable while the device is implanted within a body of a patient;
    a plurality of sensors in electrical communication with the battery, the sensors being disposed on or carried by the housing and configured to detect physiological data while the device is implanted within the patient, the sensors comprising:
        a temperature sensor;
        a pulse oximeter;
        a heart-rhythm sensor; and
        an accelerometer;
    an electronic identifier configured to enable remote electronic identification of at least one of the patient or the device;
    a data storage component disposed within the housing, the data storage component configured to store, while the device is implanted within the patient, the physiological data detected via the sensors; and
    a wireless communication component configured to transmit, while the device is implanted within the patient, physiological data stored in the data storage component to one or more external computing devices.

2. The device of claim 1, wherein the housing has a height of less than about 0.5 inches and a largest width dimension of between about 1 to 3 inches.

3. The device of claim 1, wherein the wireless communication component is configured to transmit the physiological data via Bluetooth.

4. The device of claim 1, wherein the wireless communication component is configured to transmit the physiological data to a smartphone.

5. The device of claim 1, wherein the heart rhythm sensor comprises a plurality of electrodes disposed on an external surface of the housing.

6. The device of claim 1, wherein the housing has a width-to-height ratio of greater than about 3.5.

7. The device of claim 1, wherein the housing further comprises a suture fixation structure configured to receive a suture therethrough to facilitate securing the device within a body of a patient.

8. An implantable, single-reservoir port device comprising:
    a biocompatible housing having a height of less than about 0.5 inches and a largest width dimension of between about 1 to 3 inches;
    a single fluid cavity disposed within the housing;
    a catheter connector in fluid communication with the fluid cavity, the catheter connector configured to be mated to a catheter;
    a plurality of sensors disposed on or carried by the housing and configured to detect physiological data while the device is implanted within a body of a patient, the sensors comprising at least a temperature sensor, a heart rate monitor, and a motion sensor;
    embedded identification information configured to be electronically extracted while the device is implanted within the patient, the embedded identification information including at least one of patient identification information, device identification information, or patient treatment history information; and
    a wireless communication component configured to transmit, while the device is implanted within the patient, physiological data detected via the sensors to one or more external computing devices.

9. The device of claim 8, wherein the housing has a width-to-height ratio of greater than about 3.0.

10. The device of claim 8, further comprising a catheter mated to the catheter connector such that the catheter is in fluid communication with the fluid cavity.

11. The device of claim 8, wherein the wireless communication component is configured to transmit the physiological data via Bluetooth.

12. The device of claim 8, wherein the wireless communication component is configured to transmit the physiological data to a smartphone.

13. The device of claim 8, wherein the plurality of sensors further comprises:
   a pulse oximeter;
   a heart-rhythm sensor; and
   an accelerometer.

14. The device of claim 8, wherein the housing further comprises a suture fixation structure configured to receive a suture therethrough to facilitate securing the device within the body.

15. The device of claim 8, further comprising a ridge formed in an upper surface of the housing at a position adjacent the fluid cavity.

16. An implantable, single-reservoir port device comprising:
   a housing configured to be implanted within a human patient, the housing containing a single reservoir;
   a cap adjacent the reservoir and configured to receive a needle therethrough for delivery of a fluid to the reservoir;
   a connector in fluid communication with the reservoir, the connector configured to be mated to a catheter;
   a plurality of sensors coupled to the housing and configured to detect physiological data while the device is implanted within a body of a patient, the physiological data including at least: temperature, blood oxygen level, body movement, and heart rate; and
   a wireless communication component configured to transmit, while the device is implanted within the patient, physiological data detected via the sensors to one or more external computing devices.

17. The device of claim 16, wherein the device has a width-to-height ratio of greater than 3.0.

18. The device of claim 16, wherein the device has a height of less than about 0.5 inches and a greatest width dimension of between about 1 to 3 inches.

19. The device of claim 16, further comprising a ridge formed in an upper surface of the housing adjacent the reservoir.

20. The device of claim 16, further comprising a battery disposed within the housing and in electrical communication with the sensors, wherein the battery is wirelessly rechargeable while the device is implanted within a patient.

21. The device of claim 16, further comprising a data storage component disposed within the housing, the data storage component configured to store the physiological data detected via the sensors.

* * * * *